(12) United States Patent
McConlogue et al.

(10) Patent No.: US 7,179,953 B2
(45) Date of Patent: *Feb. 20, 2007

(54) MONITORING APP CLEAVAGE IN TRANSGENIC RODENTS COMPRISING AN APP-SWEDISH MUTATION

(75) Inventors: Lisa C. McConlogue, San Francisco, CA (US); Jun Zhao, San Diego, CA (US); Sukanto Sinha, San Francisco, CA (US)

(73) Assignees: Elan Pharmaceuticals, Inc., South San Francisco, CA (US); Eli Lilly and Company, Indianapolis, IN (US)

( * ) Notice: Subject to any disclaimer, the term of this patent is extended or adjusted under 35 U.S.C. 154(b) by 363 days.

This patent is subject to a terminal disclaimer.

(21) Appl. No.: 10/609,143

(22) Filed: Jun. 27, 2003

(65) Prior Publication Data

US 2005/0022257 A1    Jan. 27, 2005

Related U.S. Application Data

(63) Continuation of application No. 09/838,556, filed on Apr. 18, 2001, now Pat. No. 6,586,656, which is a continuation of application No. 09/209,647, filed on Dec. 10, 1998, now Pat. No. 6,245,964, which is a continuation of application No. 08/785,943, filed on Jan. 22, 1997, now Pat. No. 5,850,003, which is a continuation of application No. 08/148,211, filed on Nov. 1, 1993, now Pat. No. 5,612,486, which is a continuation of application No. 08/143,697, filed on Oct. 27, 1993, now Pat. No. 5,604,102.

(51) Int. Cl.
*G01N 33/00* (2006.01)
*A01K 67/00* (2006.01)

(52) U.S. Cl. .............. 800/3; 800/12; 800/14; 800/18

(58) Field of Classification Search .......... 800/3, 800/12, 13, 18, 14; 435/320.1
See application file for complete search history.

(56) References Cited

U.S. PATENT DOCUMENTS

| | | | |
|---|---|---|---|
| 4,666,829 A | 5/1987 | Glenner et al. | |
| 4,736,866 A | 4/1988 | Leder et al. | |
| 4,873,191 A | 10/1989 | Wagner et al. | |
| 5,134,062 A | 7/1992 | Blass | |
| 5,200,339 A | 4/1993 | Abraham | |
| 5,221,607 A | 6/1993 | Cordell et al. | |
| 5,234,814 A | 8/1993 | Card et al. | |
| 5,387,742 A | 2/1995 | Cordell | |
| 5,441,870 A | 8/1995 | Seubert et al. | |
| 5,455,169 A | 10/1995 | Mullan | |
| 5,547,841 A | 8/1996 | Marotta et al. | |
| 5,580,003 A | 12/1996 | Malone et al. | |
| 5,593,846 A | 1/1997 | Schenk et al. | |
| 5,604,102 A | 2/1997 | McConlogue et al. | |
| 5,605,811 A | 2/1997 | Seubert et al. | |
| 5,612,486 A | 3/1997 | McConlogue et al. | |
| 5,721,130 A | 2/1998 | Seubert et al. | |
| 5,750,349 A | 5/1998 | Suzuki et al. | |
| 5,766,846 A | 6/1998 | Schlossmacher et al. | |
| 5,837,672 A | 11/1998 | Schenk et al. | |
| 5,850,003 A * | 12/1998 | McLonlogue et al. | 800/9 |
| 5,955,317 A | 9/1999 | Suzuki et al. | |
| 6,018,024 A | 1/2000 | Seubert et al. | |
| 6,245,964 B1 * | 6/2001 | McLonlogue et al. | 800/12 |
| 6,586,656 B2 * | 7/2003 | McLonlogue et al. | 800/3 |

FOREIGN PATENT DOCUMENTS

| | | |
|---|---|---|
| EP | 123 527 | 10/1984 |
| EP | 173 494 | 3/1986 |
| EP | 171 496 | 11/1991 |
| EP | 184 187 | 6/1992 |
| EP | 444 856 | 9/1997 |
| JP | 62-100291 | 5/1997 |
| WO | WO 86/01533 | 3/1986 |
| WO | WO 87/02671 | 5/1987 |
| WO | WO 90/12870 | 11/1990 |
| WO | WO 90/12871 | 11/1990 |
| WO | WO 91/16628 | 10/1991 |
| WO | WO 91/19810 | 12/1991 |
| WO | WO 92/00521 | 1/1992 |
| WO | WO 92/09699 | 6/1992 |
| WO | WO 92/13069 | 8/1992 |
| WO | WO 93/01817 | 3/1993 |
| WO | WO 93/21526 | 10/1993 |
| WO | WO 93/14200 | 12/1993 |
| WO | WO 94/00569 | 1/1994 |

(Continued)

OTHER PUBLICATIONS

Moreadith et al. Gene Targeting in Embryonic Stem Cell: the New Physiology and Metabolism. J. Molec. Med. 1997, vol. 75, 208-216.*

(Continued)

*Primary Examiner*—Deborah Crouch
(74) *Attorney, Agent, or Firm*—Townsend and Townsend and Crew, LLP

(57) ABSTRACT

The invention provides transgenic non-human animals and transgenic non-human mammalian cells harboring a transgene encoding an APP polypeptide comprising the Swedish mutation.

7 Claims, 5 Drawing Sheets

FOREIGN PATENT DOCUMENTS

| | | |
|---|---|---|
| WO | WO 94/01772 | 1/1994 |
| WO | WO 94/10569 | 5/1994 |
| WO | WO 94/23049 | 10/1994 |

OTHER PUBLICATIONS

Seamark, R. F. Progress and Emerging Problems in Livestock Transgenesis: a Summary Perspective. Reproduct. Fertil. DEvel.. 1994, vol. 6, pp. 653-657.*
Mullins et al. Perspective Series: Molecular Medicine in Genetically Engineered Animals, Transgenesis in the Rat and Larger Mammals. J. Clinical INvest. vol. 98, No. 11, Supp. 1996, pp. 537-540.*
Podlisny e al. Synthetic Amyloid Beta Protein Fails to Produce specific Neurotozicity in Monkey Cerebral Cortex. Neuro. Biol. Aging. 1992, vol. 13, pp. 561-567.*
"Alzheimer's Assult," *ScienceScope*, p. 1059 (Feb. 28, 1992).
Abraham et al., "A calcium-activated protease from Alzheimer's disease brain cleaves at the N-terminus of the amyloid β-protein" *Biochem. Biophys. Res. Comm.*, 174:790-796 (1991).
Ali et al., "More Transgenic Mouse Studies of Alzheimer Amyloid Precursor (APP) Proteins and Derivatives," *Society for Neuroscience Abstracts*, 18(2):abstract 616.8, from 22nd annual meeting in Anaheim, CA Oct. 25-30, 1992.
Allison et al., "Diabetes in transgenic mice resulting from overexpression of class I histocompatibility molecules in pancretic β cells," *Nature*, 333:529-533 (1988).
Antal et al., "Animal Models of Alzheimer's, Parkinson's and Huntingdon's Disease. A Minireview," *Neurobiology*, 1(2):101-122 (1993).
Bonadio et al., "Transgenic Mouse Model of the Mild Dominant Form of Osteogenesis Imperfecta," *PNAS*, 87:7145-7149 (1990).
Buxbaum et al., "Expression of APP in Brains of Transgenic Mice Containing the Entire Human App," *Gene*, 197(2):639-645 (1993).
Cai et al., "Release of excess amyloid beta protein from a mutant amyloid beta protein precursor" *Science* 259:514-516 (Jan. 22, 1993).
Cai et al., "Release of Excess Amyloid β Protein Precursor." *Science*, 259:514-516 (1993).
Ceballos-Picot et al., "Neuronal-specific expression of human copper-zinc superoxide dismutase gene in transgenic mice: animal model od gene dosage effects in Down's syndrome," *Brain Research*, 552:198-214 (1991).
Chartier-Harlan et al., "Early onset Alzheimer's disease caused by mutations at condon 717 of the β-amyloid precursor protein gene" *Nature*, 353:844-846 (1991).
Citron et al., "Mutation of the beta-amyloid precursor protein in familial Alzheimer's Disease increases beta-protein production" *Nature*, 360:672-674 (Dec. 17, 1992).
Citron et al., "Mutation of the β-amyloid precursor protein in familial Alzheimer's disease increases β-protein production," *Nature*, 360:672-674 (1992).
Cotton, R.G.H., "A G to C Transversion in Codon 258 of the α-Subunit of β-Hexosaminidase A in an Infant Tay-sachs Disease Patient," *Human Mutaion*, 2:496-497 (1993).
Crawford et al., "Alzheimer's Diesease Untangled," *BioEssays*, 14(11):727-734 (1992).
De Strooper et al., "Study of the Synthesis and Secretion of Normal and Artificial Mutants of Murine Amyloid Precursor Protein (APP): Cleavage osAPP Occurs in a Late Compartment of the Default Secretion Pathway," *J. Cell Biology*, 121(2):295-304 (1993).
Dovey et al., "Cells with a familial Alzheimer's disease mutation produce authentic β-peptide," *NeuroReport*, 4:1039-1042 (1993).
Epstein et al., "Transgenic mice with increased Cu/Zn-superoxide dismutase activitiy: Animal model of dosage effects in Down syndrome," *PNAS*, 84:8044-8048 (1987).
Erickson, D., "Model Mice, Transgenic animals aid Alzheimer's research," *Scientific American*, Sep. 1991.
Esch et al., "Cleavage of amyloid β peptide during constitutive processing of its precursor" *Science*, 248:1122-1124 (1990).
Estus et al., "Potentially amyloidogenic, carboxyl-terminal derivatives of the amyloid protein precursor" *Science*, 255:726-728 (1992).
Felsenstein et al., "Transgenic Rat and In-Vitro Studies of β-Amyloid Precursor Protein Processing," pp. 401-409 from *Alzheimer's and Parkinson's Disease*, edited by Hanin, I., Plenum Press, New York, (1995).
Fidani et al., "Screening for mutations in the open reading frame and promoter of the β-amyloid precursor protein gene in familial Alzheimer's disease: identification of a further family with APP717 Val→ 11e," *Human Molecular Genetics*, 1(3):165-168 (1992).
Fisher et al., "Expression of the amyloid precursor protein gene in mouse oocytes and embryos," *PNAS*, 88:1779-1782 (1991).
Forss-Petter et al., "Transgenic mice expressing β-galactosidase in mature neurons under neuron-specific enolase promoter control" *Neuron*, 5:187-197 (1990).
Francis et al., "Animal and Drug Modelling for Alzheimer Synaptic Pathology," *Progress in Neurobiology*, 39:517-545 (1992).
Fraser et al., "Biochemistry of Alzheimer's Disease Amyloid Plaques," *Clin. Biochem.*, 26:339-349 (1993).
Fukamizu et al., "Chimeric Renin-angiotensin System Demonstrates Sustained Increase in Blood Pressure of Transgenic Mice Carrying Both Human Renin and Human Angiotensinogen Genes," *Journal of Biological Chemistry*, 268(16):11617-11621 (1993).
Fukuchi et al., "Intestinal β-Amyloidosis in Transgenic Mice," abstract 421.16, *Society for Neuroscience Abstracts*, 19:1035 (1993).
Fukuchi et al., "Transgenic Animal Models for Alzheimer's Disease," *Annals of the New York Academy of Sciences*, 695:217-223 (1993).
Fuminori et al., "Transgenic mice for the amyloid precursor protein 695 isoform have impaired spatial memory," *NeuroReport*, 2:781-784 (1991).
Gallagher et al., "Animal models of normal aging: relationship between cognitive decline and makers in hippocampal circuitry," *Behavioural Brain Research*, 57:155-162 (1993).
Gandy et al., "Amyloidogenesis in Alzheimer's Disease: Some Possible Therapetuic Opportunities," *Trends in Pharmacological Sciences*, 13:108-113 (1992).
*Gene Targeting A Practical Approach*, edited by Joyner, A.L., Oxford Univ. Press (1993) cover page & table of contents.
Glenner et al. "Alzheimer's disease: Initial report of the purification and characterization of a novel cerebrovascular amyloid protein" *Biochem. Biophys. Res. Comm.*, 120:885-890 (1984).
Glenner et al., "Alzheimer's disease and Down's Syndrome: Sharing of unique cerebrovascular amyloid fibril protein" *Biochem. Biophys. Res. Comm.*, 122:1131-1135 (1984).
Goate et al., "Segregation of a missense mutation in the amyloid precursor protein gene with familial Alzheimer's disease" *Nature*, 349:704-706 (1991).
Goding, James W., "Production and application of monoclonal antibodies in cell biology, biochemistry and immunology" in: *Monoclonal Antibodies: Principles and Practice*, Ch. 3, pp. 56-74, Academic Press, London (1984).
Golde et al., "Processing of the amyloid protein precursor to potentially amyloidgenic derivatives" *Science*, 255:728-730 (1992).
Golde et al., "Production of Amyloid β Protein from Normal Amyloid β-Protein Precursor (βAPP) and the Mutated βAPPS Linked to Familial Alzheimer's Disease," from *Alzheimer's Disease Amyloid Precursors Proteins, Signal Transduction, and Neural Transplantaion*, vol. 695, pp. 103-108, by Annals of the New York Academy of Sciences (1993).
Goldgaber et al., "Characterization and Chromosomal Localization of a cDNA Encoding Brain Amyloid of Alzheimer's Disease," *Science*, 235:877-880 (1987).
Goverman et al., "Transgenic Mice That Express a Myelin basic Protein-Specific T Cell Receptor Develop Spontaneous Autoimmunity," *Cell*, 72:551-560 (1993).
Greaves et al., "A transgenic mouse model of sickle cell disorder," *Nature*, 343:183-185 (1990).
Greenberg et al., "Transgenic Mouse Studies of Alzheimer Amyloid Precursor (APP) Proteins and Derivatives," *Society for Neuroscience Abstracts*, vol. 18 part2, abstract 616.7 (1992).

Greenberg et al., "Yet More Transgenic Mouse Studies of Alzheimer Amyloid Precursor (APP)," *Soc. for Neurosci. Abstracts*, 19:1035, abst. 421.12 (1993).

Haass et al., "Amyloid β-peptide is produced by cultured by cells during normal metabolism" *Nature*, 359:322-325 (1992).

Haass et al., "Cellular Processing of β-Amyloid Precursor Protein and the Genesis of Amyloid β-Peptide," *Cell*, 75:1039-1042 (1993).

Hammer et al., "Partial correction of murine hereditary growth disorder by germ-line incorporation of a new gene," *Nature*, 311:65-67 (1984).

Hardy et al., "The Alzheimer family of diseases: many etiologies, one pathogenesis?," *PNAS*, 94:2095-2097 (1997).

Hardy, J., "Framing β-amyloid," *Nature Genetics*, 1:233-234 (1992).

Harris et al., "Transgenic Animals as Tools in Drug Development," *Agents & Actions* (38) Special Conference Issue, 1993.

Hendricks et al., "Presenile dementia and cerebral haemorrhage linked to a mutation at codon 692 of the β-amyloid precursor protein gene," *Nature Genetics*, 1:218-221 (1992).

Higgins et al., "Transgenic mice expressing human β-APP751, but not mice expressing β-APP695, display early Alzheimer's disease-like histophathology" *Annals NY Acad. Sci.*, 695:224-227 (1993).

Higgins et al., "Transgenic mouse brain histopathology resembles early Alzheimer's disease" *Ann. Neurol.*, 35:598-607 (1994).

Hogan et al., *Manipulating the Mouse Embryo, A Laboratory Manual*, Cold Spring Harbor Laboratory, (1986) cover page and table of contents.

Holtzman et al., "Molecular studies in Alzheimer's disease," *TIBS*, 16:140-144 (1991).

Howland et al., "Neuron-Specific Expression of Human Beta-Amyloid Precursor Protein (APP) In Transgenic Mice," *Society for Neuroscience Abstracts*, 19:1035, abstract 421.13 (1993).

Hsiao et al., "Spontaneous Neurodegeneration in Transgenic Mice with Mutant Prion Protein," *Science*, 250:1587-1590 (1990).

Hyman et al., "Amyloid dementia and Alzheimer's disease," *Curr. Opin. Neuorlogy Neurosurgery*, 5:88-92 (1992).

Hyman et al., "Kunitz protease inhibitor-containing amyloid β-protein precursor immunoreactivity in Alzheimer's disease" *J. Neuropath. Exp. Neurol.*, 51:76-83 (1992).

Iwamoto et al., "Neuroblastoma in a transgenic mouse carrying a metallothionein/ *ret* fusion gene," *Br. J. Cancer*, 67:504-507 (1993).

Jan et al., "Receptor-regulated ion channels," *Curr. Opin. Cell Biology*, 9:155-160 (1997).

Jones et al., "Mutation in codon 713 of the β amyloid precursor protein gene presenting with schizophrenia," *Nature Genetics*, 1:306-309 (1992).

Kammesheidt et al., "Deposition of β/A4 immunoreactivity and neural pathology in transgenic mice expressing the carboxyl-terminal fragment of the alzheimer Amyloid precursor in the brain," *PNAS*, 89:10857-10861 (1992).

Kang et al., "The precursor of Alzheimer's disease amyloid A4 protein resembles a cell-surface receptor" *Nature*, 325:733-736 (1987).

Keffer et al., "Transgenic mice expressing human tumor necrosis factor: a predictive genetic model of arthritis," *EMBO J.*, 10(13):4025-4031 (1991).

Kennedy et al., "Familial Alzheimer's disease," *Brain*, 116:309-324 (1993).

Kennedy et al., "Only Kuntiz-inhibitor-containing isoforms of secreted Alzheimer amyloid precursor protein show amyloid immunoreactivity in normal cerebrospinal fluid" *Neurodegeneration*, 1:59-64 (1992).

Kitaguchi et al., "Novel precursor of Alzheimer's disease amyloid protein shows protease inhibitory activity" *Nature*, 331:530-532 (1988).

Koliatsos et al., "Neurotrophic Strategies for Treating Alzheimer's Disease: Lessons from Basic Neurobiology and Animal Models," from *Alzheimer's Diisease Amyloid Precursor Proteins, Signal Transduction, and Neural Transplantation*, vol. 695, pp. 292-299, by Annals of the New York Academy of Sciences (1993).

Konig et al., "Identification and Differential Expression of a Novel Alternative Splice Isoform of the βA4 Amyloid Precursor Protein (APP) mRNA in Leukocytes and Brain Microglial Cells," *J. Biol. Chem.*, 267(15):10804 (1992).

Korf et al., "S-Antigen and Rod-Opsin Immunoreactions in Midline Brain Neoplasms of Transgenic Mice: Similarities to Pineal Cell Tumors and Certain Medulloblastomas in Man," *J. Neuropath. Exper. Neulogy*, 49(4):424-437 (1990).

Kozak, M., "The Scanning Model for Translation: An Update," *J. Cell Biology*, 108:229-241 (1989).

Kozlowski et al., "the Neurotoxic Carboxy-Terminal Fragment of the Alzheimer Amyloid Precursor Binds Specificity to a Neuronal Cell Surface Molecule: pH Dependance of the Neurotoxicity and the Binding," *J. Neuroscience*, 12(5):1679-1687 (1992).

Lamb et al., "Introduction and expression of the 400 kilobase *precursor amyloid protein* gene in transgenic mice," *Nature Genetics*, 5:22-30 (1993).

Lannfelt et al., "Low frequency of the APP 670/671 mutation in familial Alzheimer's disease in Sewden," *Neuroscience Letters*, 153:85-87 (1993).

Lavigueur et al., "High Incidence of Lung, Bone, and Lymphoid Tumors in Transgenic Mice Overexpressing Mutant Alleles of the p53 Oncogene," *Mol. Cellular Biol.*, 9(9):3982-3991 (1989).

Levy et al., "Mutation of the Alzheimer's Amyloid Gene in Hereditary Cerebral Hemorrhage, Dutch Type," *Science*, 248:1124-1126 (1990).

Lieberburg et al., "Expression of Human Alzheimer's Amyloid Precursor Protein In Transgenic Mice," *Soc. Neuroscience Abstracts*, vol. 19, abstract 421.15 (1993).

Luo et al., "Humasn Amyloid Precursor Protein Behavior Deficit of Flies Deleted for Appl Gene," *Neuron*, 9:595-605 (1992).

Marx, J., "Alzheimer's Research Moves to Mice," *Science*, 253:266-267 (1991).

Marx, J., "Major Setback for Alzheimer's Models," *Science*, 255:1200-1202 (1992).

Marx, J., "New Lead to an Alzheimer's Mouse?," *Science*, 261:1520 (1993).

Merlino, Glenn T., "Transgenic Animals in Biomedical Research," *Faseb J*, 5:2996-3001.

Miller et al., "Alzheimer's disease: transgenic models to test new chemicals and pharmaceuticals," *Curr. Opin. Biotechnology*, 3:683-686 (1992).

Moran et al., "Age-related learning deficits in transgenic mice expressing the 751-amino acid isoform of human β-amyloid precursor protein," *PNAS*, 92:5341-5345 (1995).

Mullan et al., "A pathenogenic mutation for probable Alzheimer's disease in the APP gene at the N-terminus of β-amyloid" *Nature Genetics*, 1:345-347 (01992).

Mullan et al., Genetic and molecular advances in Alzheimer's disease, *TINS*, 16(10):398-403 (1993).

Mullan, M., "Familial Alzheimer's disease: second gene locus located," *BMJ*, 305:1108-1109 (1992).

Mullins et al., "Fulminant hypertension in transgenic rats harbouring the mouse *Ren-2* gene," *Nature*, 344:541-544 (1990).

Murrell et al., "A mutation in the amyloid precursor protein associated with hereditary Alzheimer's disease" *Science*, 254:97-99 (1991).

Narisawa et al., "Transgenic Mice Expressing the Tumor Marker Germ Cell Alkaline Phosdphatase: An In Vivo Tumor Model for Human Cancer Antigens," *PNAS*, 90:5081-5085 (1993).

Neve et al., "Brain transplants of cells expressing the carboxyl-terminal fragment of the Alzheimer amyloid protein precursor cause specific neuropathology *in vivo*," *PNAS*, 89:3448-3452 (1992).

Nussbaum et al., "Alzheimer's Disease and Amyloid Protein—in (Transgenic) Mice and Men," *Harefuah*, 123(9):362-364, document in Hebrew (1992).

Oltersdorf et al., "The Alzheimer's amyloid precursor protein: Identification of a stable intermediate in the biosynthetic/degradative pathway" *J. Biol. Chem.*, 265:4492-4497 (1990).

Oltersdorf et al.,"The secreted form of the Alzheimer's amyloid precursor protein with the Kunitz domain is protease nexin-II" *Nature*, 341:144-147 (1989).

Order Denying Mayo's Ex Patre Motion to Stay Deadline for Motion for Attorney's Fees, US District Court for the Northern District of California, Case No. C99-04464 WHA.

Order Granting Defendant's Motion for Summary Judgment of Anticipation, US District Court for the Northern District of California, Case No. C99-04464 WHA.

Palmert et al., "Soluble derivatives of the β amyloid protein precursor of Allzheimer's disease are labeled by antisera to the β amyloid protein" Biochem. Biophys. Res. Comm., 165:182-188 (1989).

Palmert et al., "The β-amyloid protein precursor of Alzheimer's disease has soluble derivatives found in human brain and cerebrospinal fluid" Proc. Natl. Acad. Sci., USA 86:6338-6342 (1989).

Palmiter et al., "Dramatic growth of mice that develop from eggs microinjected with metallathionein-growth hormone fusion genes," Nature, 300:611-615 (1982).

Palvin, R., "Brain Amyloid in Alzheimer's Disease—A New Experimental Model," Neurologia Croatica, 41(4):227-234 (1992).

Pearson et al., "Expression of the human β-amyloid precursor protein gene from a yeast artificial chromosome in transgenic mice," PNAS, 90:10578-10582 (1993).

Perraud et al., "The promoter of the human cystic fibrosis transmembrand conductance regulator gene directing SV-40 T antigen expression induces malignant proliferation of ependymal cells in transgenic mice," Oncogene, 7:993-997 (1992).

Ponte et al., "A new A4 amyloid mRNA contains a domain homologous to serine proteinase inhibitors" Nature, 331:525-527 (1988).

Price et al., "Alzheimer's Disease-Type Brain Abnormalities in Animal Models," Down Syndrome and Alzheimer Disease, pp. 271-287, Wiley-Liss, Inc., (1992).

Pullian et al.,"Use of aggregating brain cultures to study the replication of herpes simplex virus types 1 and 2 in central nervous system tissue" J. Virol. Met., 9:301-316 (1984).

Quon et al., "Formation of β-amyloid deposits in brains of transgenic mice" Nature, 352:239-241 (1991).

Quon et al., "Formation of β-amyloid protein deposits in brains of transgenic mice," Nature, 352:239-241 (1991).

Roakis et al., "An Alternative secretase cleavage produces soluble Alzheimer amyloid precursor protein containing a potentially amyloidogenic sequence" Soc. Neurosci., Abstract No. 15.5 (Oct. 26, 1993) Anaheim, CA.

Robakis et al., "Molecular cloning and characterization of a cDNA encoding the cerebrovascular and the neuritic plaque amyloid peptides," PNAS, 84:4190-4194 (1987).

Roche et al., "Biologically Active Domain of the Secreted Form of the Amyloid β/A4 Protein Precursor," from Alzheimer's Disease Amyloid Precursor Proteins, signal Transduction, and Neuronal Transplantation, Annals of the New York Academy of Sciences, vol. 695, pp. 149-157 (1993).

Ryan et al., "Human Sickle Hemoglobin in Transgenic Mice," Science, 247:566-568 (1990).

Sahasrabudhe et al., "Release of Amino-terminal Fragments from Amyloid Precursor Protein Reporter and Mutated Derivatives in Cultured Cells," J. Biol. Chemistry, 267(15):25602-25608 (1992).

Sandhu et al., "Expression of the Human β-Amyloid Protein of Alzheimer's Disease Specfically in the Brains of Transgenic Mice," J. Biol. Chemistry, 266(32):21331-21334 (1991).

Sarvetnick et al., "Insulin-Dependant diabetes Mellitus Induced in Transgenic Mice by Ectopic Expression of Class II MHC and Interferon-Gamma," Cells, 52:773-782 (1988).

Savage et al., "Human Amyloid Precursor Protein Expression in Transgenic Mice as a Model of Alzheimer's Disease: Search for pathology," abstract 421.14, Society for Neuroscience Abstracts, 19:1035 (1993).

Scott et al., "Inability to Detect β-Amyloid Protein Precursor mRNA in Alzheimer Plaque-Associated Microglia," Experimental Neurology, 121:113-118 (1993).

Scott et al., "The Processing of Native and Mutant APP751 in Human 293 Cells," Neurobiology of Aging, 13(supp. 1):578-579, abstract 310 (1992).

Scott et al., "Transgenic Mice Expressing Hamster Prion Protein Produce Species-Specific Scrapie Infeectivity and Amyloid Plaques," Cell, 59:847-857 (1989).

Selkoe et al., "Physiological production of the β-amyloid protein and the mechanisms of Alzheimer's disease" Trends Neurosci., 16 (10):403-409 (Oct. 1993).

Selkoe et al., "Physiological production of the β-amyloid protein and the mechanisms of Alzheimer's disease," Trends in Neuroscience, 16(10):403-409 (1993).

Selkoe et al., "β-amyloid precursor protein of Alzheimer disease occurs as 110- to 135-kilodalton membrane-associated proteins in neural and nonneural tissue" Proc. Natl. Acad. Sci., USA 85:7341-7345 (1988).

Seubert et al., "Isolation and quantification of soluble Alzheimer's β-peptide from biological fluids" Nature, 359:325-327 (1992).

Seubert et al., "Secretion of β-amyloid precursor protein cleaved at the amino terminus of the β amyloid peptide" Nature, 361:260-263 (1993).

Siman et al., "Processinf of the β-Amyloid Precursor Multiple Proteases Generates and Degrade Potentially Amyloidogenic Fragments," J. Biol. Chemistry, 268(22):16602-16609 (1993).

Sisodia, S.S., "β-Amyloid precursor protein cleavage by a membrane-bound protease," PNAS, 6075-6079 (1992).

Society for Neuroscience, Abstracts, vol. 19, Part 2, 23rd Annual Meeting, Washington, DC, Nov. 7-12, 1993.

Society for Neuroscience Abstracts, vol. 18, Part 2, 22nd Annual Meeting, Anaheim, California, Oct. 25-30, 1992.

Sofroniew et al., "Transgenic modelling of neurodgenerative events gathers momentum," TINS, 14(12):513 (1991).

Stacey et al., "Perinatal lethal osteogenesis imperfecta in transgenic mice bearing an engineered mutation pro-α1(I) collagen gene," Nature, 332:131-136 (1988).

Stout et al., "Expression of human HPRT in the central nervous system of transgenic mice," Nature, 317:250 (1985).

Supplement 1 to vol. 15 of Journal "Neurobiology of Aging", Research on Age-Related Phenomena, Neurodegeneration and Neuropathology, Abstract 49.

Tanzi et al., "Amyloid β Protein Gene:cDNA, MRNA Distibution, and Genetic Linkage Near the Alzheimer Locus," Science, 235:880-884 (1987).

Tanzi et al., "Protease inhibitor domain encoded by an amyloid protein precursor mRNA associated with Alzheimer's disease," Nature, 331:528-530 (1998).

Tomita et al., "The presenilin 2 mutation (N1411) linked to familial Azheimer disease (Volga German families) increases the secretion of amyloid β protein ending at the 42nd (or 43rd) residue," PNAS, 94:2025-2030 (1997).

Travis, J., :New Piece in Alzheimer's Puzzle, Science, 261:828-829 (1993).

Travis, J., "New Price in Alzheimer's Puzzle," Science, 261:828-829 (1993).

Usami et al., "The Triplets of Lysine Residues (Lys724-Lys725-Lys726) of Alzheimer's Amyloid Precursor protein Plays an Important Role in membrane Anchoarge and Processing," J. Neurochem., 61(1):239-246 (1993).

Van Duijn et al., "Genetic transmission of Alzheimer's disease among families in a Dutch population based study," J. Med. Genet., 30:640-646 (1993).

Wang et al., "Tissue- and Development-specific Expression of the Human Phenylalanine Hydroxylase/Chloramphenicol Acetyltransferase Fusion Gene in Transgenic Mice," J. Boilogical Chemistry, 267(21):15105-15110 (1992).

Weidemann et al., "Identification, biogenesis, and localization of precursors of Alzheimer's disease A4 amyloid protein" Cell, 57:115-126 (1989).

Wells et al., "Human dystrophin expression corrects the myopathic phenotype in trangenic mdx mice," Human Molecular Genetics, 1(1):35-40 (1992).

Westphal, H., "Mouse models of human disease,". Curr Opin Biotech., 2:830-833 (1991).

Wiedlocha et al., "Dual Mode of signal Transduction by Externally Added Acidic Fibroblast Growth Factor," Cell, 76:1039-1051 (1994).

Wirak et al., "Age-Associated Inclusions in Normal and Transgenic Mouse Brain," *Science*, 255:1443-45 (11992).

Wirak et al., "Deposits of Amyloid β Protein in the Central Nervous system of Trangenic Mice," *Science*, 253:323-325 (1991).

Wirak et al., "Regulatory region of human amyloid precursor protein (APP) gene promotes neuron-specific gene expression in the CNS of transgenic mice," *EMBO*, 10(2):289-296 (1991).

Yamaguchi, "Transgenic mice for the amyloid precursor protein 695 isoform have impaired spatial memory," *NeuroReport*, 2(12):781-784 (1991).

Yanker et al., "Neurotoxicity of a Fragment of the Amyloid Precursor Associated with Alzheimer's Disease," *Science*, 245:417-420 (1989).

Priority Document for PCT/US93/01817, U.S. Appl. No. 07/965,971 filed Oct. 26, 1992.

Declaration of Dora Games in Opposition to European Patent 730 643.

Games et al., "Evidence of Altered APP Processing Following Acute Head Trauma in the Rodent," *Society For Neuroscience Abstracts*, 18(20):1437, abstract 601.2 from 22nd annual meeting held in Anaheim, CA on Oct. 25-30, 1992.

Kawabata et al., "Amyloid plaques, neurofibrillary tangles and neuronal loss in brains of transgenic mice overexpressing a C-terminal fragment of human amyloid precursor protein," *Nature*, 354:476-478 (1991).

Kawabata, S., "Alzheimer's retraction," *Nature*, 356:23 (1992).

McConlogue et al., "Transgenic Mice Expressing Human Alzheimer's B-Amyloid Precursor Protein Product High Amounts of B-Peptide," *Neurobiology of Aging*, 15 (suppl. 1):S12, abstract 49 from 4th Int. Conf. on Alzheimer's Disease and Related Disorders, held Jul. 29-Aug. 3, 1994 in Minneapolis, MN.

Minutes of Oral Proceedings in Opposition to European application 94931891.9 (May 8, 2006).

Online European Patent Register - Results for European application number 19940913347 (Aug. 26, 2002).

Selkoe, D. J., "In the Beginning . . .," *Nature*, 354:432-433 (1991).

Terai et al., "β-Amyloid Deposits in Transgenic Mice Expressing Human β-Amyloid Precursor Protein Have the Same Characteristics as Those in Alzheimer's Disease," *Neuroscience*, 104(2):299-310 (2001).

\* cited by examiner

Ab Swe 192

MONITORING APP CLEAVAGE IN TRANSGENIC RODENTS COMPRISING AN APP-SWEDISH MUTATION

CROSS-REFERENCE TO RELATED APPLICATION

This application is a continuation-in-part of application Ser. No. 08/143,697 filed 27 Oct. 1993, the disclosure of which is specifically incorporated herein by reference.

TECHNICAL FIELD

The invention provides transgenic non-human animals and transgenic non-human mammalian cells harboring a transgene encoding an amyloid precursor protein (APP) comprising the Swedish mutation (lysine$^{595}$-methionine$^{596}$ mutated to asparagine$^{595}$-leucine$^{596}$); the invention also provides non-human animals and cells comprising a transgene encoding an APP comprising the Swedish mutation and further comprising functionally disrupted endogenous APP gene loci, transgenes and targeting constructs used to produce such transgenic cells and animals, transgenes encoding human Swedish mutation APP polypeptide sequences, and methods for using the transgenic animals in pharmaceutical screening and as commercial research animals for modeling neurodegenerative diseases (e.g., Alzheimer's disease) and APP biochemistry in vivo.

BACKGROUND OF THE INVENTION

Alzheimer's disease (AD) is a progressive disease known generally as senile dementia. Broadly speaking the disease falls into two categories, namely late onset and early onset. Late onset, which occurs in old age (65+ years), may be caused by the natural atrophy of the brain occurring at a faster rate and to a more severe degree than normal. Early onset AD is much more infrequent but shows a pathologically identical dementia with brain atrophy which develops well before the senile period, i.e., between the ages of 35 and 60 years.

Alzheimer's disease is characterized by the presence of numerous amyloid plaques and neurofibrillary tangles (highly insoluble protein aggregates) present in the brains of AD patients, particularly in those regions involved with memory and cognition. While in the past there was significant scientific debate over whether the plaques and tangles are a cause or are merely the result of AD, recent discoveries indicate that amyloid plaque is a causative precursor or factor. In particular, it has been discovered that the production of β-amyloid peptide, a major constituent of the amyloid plaque, can result from mutations in the gene encoding amyloid precursor protein, a protein which when normally processed will not produce the β-amyloid peptide. It is presently believed that a normal (non-pathogenic) processing of the β-amyloid precursor protein occurs via cleavage by a putative "α-secretase" which cleaves between amino acids 16 and 17 of the protein. It is further believed that pathogenic processing occurs via a putative "β-secretase" at the amino-terminus of the β-amyloid peptide within the precursor protein. Moreover, β-amyloid peptide appears to be toxic to brain neurons, and neuronal cell death is associated with the disease.

β-amyloid peptide (also referred to as A4, βAP, Aβ, or AβP; see, U.S. Pat. No. 4,666,829 and Glenner and Wong (1984) *Biochem. Biophys. Res. Commun.* 120: 1131) is derived from β-amyloid precursor protein (βAPP), which is expressed in differently spliced forms of 695, 751, and 770 amino acids. See, Kang et al. (1987) *Nature* 325: 773; Ponte et al. (1988) *Nature* 331: 525; and Kitaguchi et al. (1988) *Nature* 331: 530. Normal processing of amyloid precursor protein involves proteolytic cleavage at a site between residues Lys$^{16}$ and Leu$^{17}$ (as number d for the vAP region where Asp$^{597}$ is residue 1 in Kang et al. (1987)), supra, near the transmembrane domain, resulting in the constitutive secretion of an extracellular domain which retains the remaining portion of the β-amyloid peptide sequence (Esch et al. (1990) *Science* 248:1122–1124). This pathway appears to be widely conserved among species and present in many cell types. See, Weidemann et al. (1989) *Cell* 57:115–126 and Oltersdorf et al. (1990) *J. Biol. Chem.* 265:4492–4497. This normal pathway cleaves within the region of the precursor protein which corresponds to the β-amyloid peptide, thus apparently precluding its formation. Another constitutively secreted form of βAPP has been noted (Robakis et al. Soc. Neurosci. Oct. 26, 1993, Abstract No. 15.4, Anaheim, Calif.) which contains more of the βAP sequence carboxy terminal to that form described by Esch et al. supra.

Golde et al. (1992) *Science* 255:728–730, prepared a series of deletion mutants of amyloid precursor protein and observed a single cleavage site within the β-amyloid peptide region. Based on this observation, it was postulated that β-amyloid peptide formation does not involve a secretory pathway. Estus et al. (1992) *Science* 255:726–728, teaches that the two largest carboxy terminal proteolytic fragments of amyloid precursor protein found in brain cells contain the entire β-amyloid peptide region.

Recent reports show that soluble β-amyloid peptide is produced by healthy cells into culture media (Haass et al. (1992) *Nature* 359:322–325) and in human and animal CSF (Seubert et al. (1992) *Nature* 359:325–327). Palmert et al. (1989) Biochm. Biophys. Res. Comm. 165:182–188, describes three possible cleavage mechanisms for βAPP and presents evidence that βAPP cleavage does not occur at methionine$^{596}$ in the production of soluble derivatives of βAPP. U.S. Pat. No. 5,200,339, discusses the existence of certain proteolytic factor(s) which are putatively capable of cleaving βAPP at a site near the βAPP amino-terminus.

The APP gene is known to be located on human chromosome 21. A locus segregating with familial Alzheimer's disease has been mapped to chromosome 21 (St. George Hyslop et al (1987) *Science* 235:885) close to the APP gene. Recombinants between the APP gene and the AD locus have been previously reported (Schellenberg et al. (1988) *Science* 241: 1507; Schellenberg et al. (1991) *Am. J. Hum. Genetics* 48: 563; Schellenberg et al. (1991) *Am. J. Hum. Genetics* 49: 511, incorporated herein by reference).

The identification of mutations in the amyloid precursor protein gene which cause familial, early onset Alzheimer's disease is evidence that amyloid metabolism is the central event in the pathogenic process underlying the disease. Four reported disease-causing mutations include with respect to the 770 isoform, valine$^{717}$ to isoleucine (Goate et al. (1991) *Nature* 349: 704), valine$^{717}$ to glycine (Chartier Harlan et al. (1991) *Nature* 353: 844), valine$^{717}$ to phenylalanine (Murrell et al. (1991) *Science* 254: 97) and with respect to the 695 isoform, a double mutation changing lysine$^{595}$-methionine$^{596}$ to asparagine$^{595}$-leucine$^{596}$ (Mullan et al. (1992) *Nature Genet* 1: 345; Citron et al. (1992) *Nature* 360: 672) referred to as th Swedish mutation. APP alleles which are positively correlated with AD are termed "disease-associated alleles".

The development of experimental models of Alzheimer's disease that can be used to define further the underlying biochemical events involved in AD pathogenesis would be highly desirable. Such models could presumably be employed, in one application, to screen for agents that alter the degenerative course of Alzheimer's disease. For example, a model system of Alzheimer's disease could be used to screen for environmental factors that induce or accelerate the pathogenesis of AD. In contradistinction, an experimental model could be used to screen for agents that inhibit, prevent, or reverse the progression of AD. Presumably, such models could be employed to develop pharmaceuticals that are effective in preventing, arresting, or reversing AD.

Unfortunately, only humans and aged non-human primates develop any of the pathological features of AD; the expense and difficulty of using primates and the length of time required for developing the AD pathology makes extensive research on such animals prohibitive. Rodents do not develop AD, even at an extreme age. It has been reported that the injection of β-amyloid protein (βAP) or cytotoxic βAP fragments into rodent brain results in cell loss and induces an antigenic marker for neurofibrillary tangle components (Kowall et al. (1991) *Proc. Natl. Acad. Sci. (U.S.A.)* 88: 7247). Mice which carry an extra copy of the APP gene as a result of partial trisomy of chromosome 16 die before birth (Coyle et al. (1988) *Trends in Neurosci.* 11: 390). Since the cloning or the APP gene, there have been several attempts to produce a mouse model for AD using transgenes that include all or part of the APP gene, unfortunately much of the work remains unpublished since the mice were nonviable or failed to show AD-like pathology. At least two published reports were retracted because of irregularities in reported results (Marx J *Science* 255: 1200; Wirak et al. (1991) *Science* 253: 323; Kawabata et al. (1991) *Nature* 354: 476; Kawabata et al. *Nature* 356: 23; Quon et al. (1991) *Nature* 352: 239; Marx *Science* 259: 457).

Thus, there is a need in the art for transgenic nonhuman animals harboring an intact disease-associated APP gene, either a human disease-associated allele such as a polynucleotide encoding a human APP protein comprising the Swedish mutation, or a complete genomic copy (or minigene) of the Swedish mutation APP gene.

Alternatively, a mutated rodent (e.g., murine) allele which comprises sequence modifications which correspond to a human APP sequence comprising the Swedish mutation can be substituted. Cell strains and cell lines (e.g., astroglial cells) derived from such transgenic animals would also find wide application in the art as experimental models for developing AD therapeutics and as a convenient source of APP protein comprising the Swedish mutation. Moreover, transgenic non-human animals comprising a transgene encoding a Swedish mutation APP protein and lacking functional endogenous APP gene loci (i.e., having an APP "knockout" background) would be a convenient source of Swedish mutation APP protein in a backgound lacking other APP proteins that do not comprise the Swedish mutation.

Based on the foregoing, it is clear that a need exists for nonhuman cells and nonhuman animals harboring one or more transgenes encoding an APP gene comprising the Swedish mutation. Thus, it is an object of the invention herein to provide methods and compositions for transferring transgenes and homologous recombination constructs into mammalian cells, especially into embryonic stem cells. It is also an object of the invention to provide transgenic nonhuman cells and transgenic nonhuman animals harboring one or more Swedish mutation APP transgenes of the invention. Of further interest to the present invention are the application of such transgenic animals as in vivo systems for screening candidate drugs for the ability to inhibit or prevent the production of pathogenic β-amyloid plaque. It would be desirable to provide methods and systems for screening test compounds for the ability to inhibit or prevent the conversion of amyloid precursor protein to pathogenic β-amyloid peptide. In particular, it would be desirable to base such methods and systems on metabolic pathways which have been found to be involved in such conversion, where the test compound would be able to interrupt or interfere with the metabolic pathway which leads to conversion. Such methods and transgenic animals should provide rapid, economical, and suitable for screening large numbers of test compounds.

The references discussed herein are provided solely for their disclosure prior to the filing date of the present application. Nothing herein is to be construed as an admission that the inventors are not entitled to antedate such disclosur by virtue of prior invention.

SUMMARY OF THE INVENTION

In accordance with the foregoing objects, in one aspect of the invention are provided nonhuman animals harboring at least one copy of a transgene conmprising a polyncleotide sequence which encodes a heterologous APP polypeptide comprising the Swedish mutation (asparagine$^{595}$-leucine$^{596}$) operably linked to a transcription regulatory sequence capable of producing expression of the heterologous APP polypeptide in the transgenic nonhuman animal. Said heterologous APP polypeptide comprising the Swedish mutation generally is expressed in cells which normally express the naturally-occurring endogenous APP gene (if present). Typically, the nonhuman animal is a mouse and the heterologous APP gene is a human Swedisch mutation APP gene. Such transgenes typically comprise a Swedish mutation APP expression cassette, wherein a linked promoter and, preferably, an enhancer drive expression of structural sequences encoding a heterologous APP polypeptide comprising the Swedish mutation.

The invention also provides transgenes comprising a gene encoding a Swedish mutation APP, said gene operably linked to a transcription regulatory sequence functional in the host transgenic animal (e.g., a neural-specific promoter). Such transgenes are typically integrated into a host chromosomal location by nonhomologous integration. The transgenes may further comprise a selectable marker, such as a neo or gpt gene operably linked to a constitutive promoter, such as a phosphoglycerate kinase (pgk) promoter or HSV tk gene promoter linked to an enhancer (e.g., SV40 enhancer).

The invention further provides nonhuman transgenic animals, typically nonhuman mammals such as mice, which harbor at least one copy of a transgene or targeting construct of the invention, either homologously or nonhomologously integrated into an endogenous chromosomal location so as to encode a Swedish mutation APP polypeptide. Such transgenic animals are usually produced by introducing the transgene or targeting construct into a fertilized egg or embryonic stem (ES) cell, typically by microinjection, electroporation, lipofection, or biolistics. The transgenic animals express the Swedish mutation APP gene of the transgene (or homologously recombined targeting construct), typically in brain tissue. Such animals are suitable for use in a variety of disease model and drug screening uses, as well as other applications.

The invention also provides nonhuman animals and cells which harbor at least one integrated targeting construct that functionally disrupts an endogenous APP gene locus, typically by deleting or mutating a genetic element (e.g., exon sequence, splicing signal, promoter, enhancer) that is required for efficient functional expression of a complete gene product.

The invention also provides transgenic nonhuman animals, such as a non-primate mammal, that have at least one inactivated endogenous APP allele, and preferably are homozygous for inactivated APP alleles, and which are substantially incapable of directing the efficient expression of endogenous (i.e., wildtype) APP. For example, in a preferred embodiment, a transgenic mouse is homozygous for inactivated endogenous APP alleles and is substantially incapable of producing murine APP encoded by a endogenous (i.e., naturally-occurring) APP gene. Such a transgenic mouse, having inactivated endogenous APP genes, is a preferred host recipient for a transgene encoding a heterologous APP polypeptide, preferably a human Swedish mutation APP polypeptide. For example, human APP comprising the Swedish mutation may be encoded and expressed from a heterologous transgene(s) in such transgenic mice. Such heterologous transgenes may be integrated in a nonhomologous location in a chromosome of the nonhuman animal, or may be integrated by homologous recombination or gene conversion into a nonhuman APP gene locus, thereby effecting simultaneous knockout of the endogenous APP gene (or segment thereof) and replacement with the human APP gene (or segment thereof).

DEFINITIONS

Figure 1A:
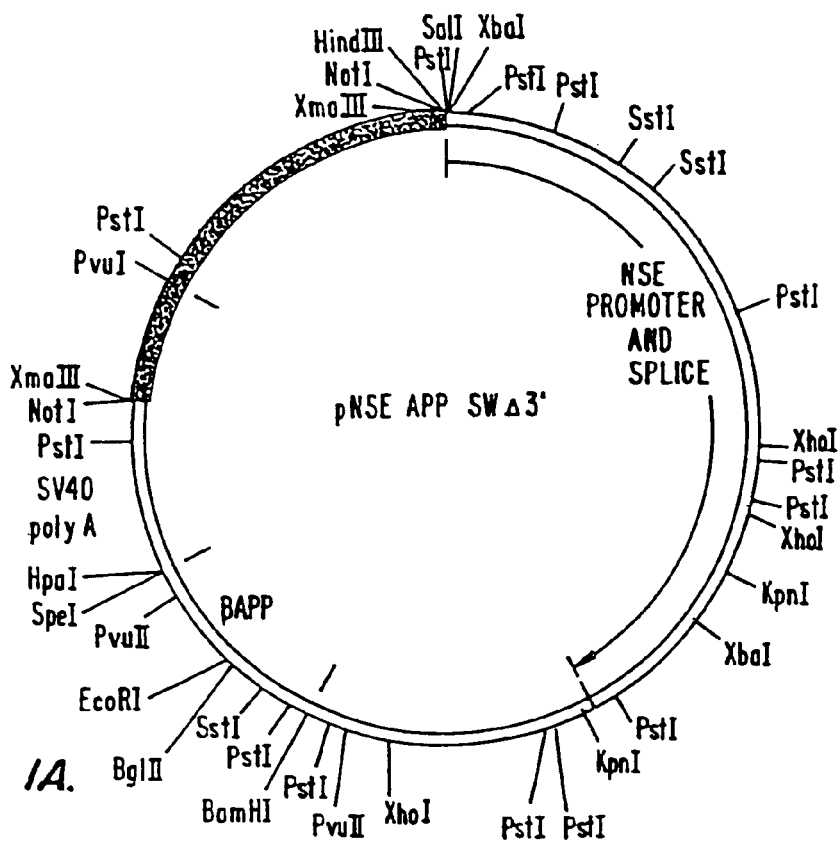
FIG. 1, panels A and B are plasmid maps of pNSEA-PPswΔ3' and pNSEAPPsw, respectively, which are used to produce transgenic mice as described herein.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The terms "substantially corresponds to", "substantially homologous", or "substantial identity" as used herein denotes a characteristic of a nucleic acid sequence, wherein a nucleic acid sequence has at least 70 percent sequence identity as compared to a reference sequence, typically at least 85 percent sequence identity, and preferably at least 95 percent sequence identity as compared to a reference sequence. The percentage of sequence identity is calculated excluding small deletions or additions which total less than 25 percent of the reference sequence. The reference sequence may be a subset of a larger sequence, such as a portion of a gene or flanking sequence, or a repetitive portion of a chromosome. However, the reference sequence is at least 18 nucleotides long, typically at least 30 nucleotides long, and preferably at least 50 to 100 nucleotides long. "substantially complementary" as used herein refers to a sequence that is complementary to a sequence that substantially corresponds to a reference sequence.

Specific hybridization is defined herein as the formation of hybrids between a targeting transgene sequence (e.g., a polynucleotide of the invention which may include substitutions, deletion, and/or additions) and a specific target DNA sequence (e.g., a human APP gene sequence), wherein a labeled targeting transgene sequence preferentially hybridizes to the target such that, for example, a single band corresponding to a restriction fragment of a gene can be identified on a Southern blot of DNA prepared from cells using said labeled targeting transgene sequence as a probe. It is evident that optimal hybridization conditions will vary depending upon the sequence composition and length(s) of the targeting transgene(s) and endogenous target(s), and the experimental method selected by the practitioner. Various guidelines may be used to select appropriate hybridization conditions (see, Maniatis et al., *Molecular Cloning: A Laboratory Manual* (1989), 2nd Ed., Cold Spring Harbor, N.Y. and Berger and Kimmel, *Methods in Enzymology, Volume 152, Guide to Molecular Cloning Techniques* (1987), Academic Press, Inc., San Diego, Calif., which are incorporated herein by reference.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. As used herein, laboratory strains of rodents which may have been selectively bred according to classical genetics are considered naturally-occurring animals.

The term "cognate" as used herein refers to a gene sequence that is evolutionarily and functionally related between species. For example but not limitation, in the human genome, the human immunoglobulin heavy chain gene locus is the cognate gene to the mouse immunoglobulin heavy chain gene locus, since the sequences and structures of these two genes indicate that they are highly homologous and both genes encode a protein which functions to bind antigens specifically.

As used herein, the term "xenogenic" is defined in relation to a recipient mammalian host cell or nonhuman animal and means that an amino acid sequence or polynucleotide sequence is not encoded by or present in, respectively, the naturally-occuring genome of the recipient mammalian host cell or nonhuman animal. Xenogenic DNA sequences are foreign DNA sequences; for example, a human APP gene is xenogenic with respect to murine ES cells; also, for illustration, a human cystic fibrosis-associated CFTR allele is xenogenic with respect to a human cell line that is homozygous for wild-type (normal) CFTR alleles. Thus, a cloned murine nucleic acid sequence that has been mutated (e.g., by site directed mutagenesis) is xenogenic with respect to the murine genome from which the sequence was originally derived, if the mutated sequence does not naturally occur in the murine genome.

As used herein, a "heterologous gene" or "heterologous polynucleotide sequence" is defined in relation to the transgenic nonhuman organism producing such a gene product. A heterologous polypeptide, also referred to as a xenogeneic polypeptide, is defined as a polypeptide having an amino acid sequence or an encoding DNA sequence corresponding to that of a cognate g n found in an organism not consisting of the transgenic nonhuman animal. Thus, a transgenic mouse harboring a human APP gene can be described as harboring a heterologous APP gene. A transgene containing various gene segments encoding a heterologous protein s quence may be readily identified, e.g. by hybridization or DNA sequencing, as being from a species of organism other than the transgenic animal. For example, expression of human APP amino acid sequences may be detected in the transgenic nonhuman animals of the invention with antibodies specific for human APP epitopes encoded by human AP gene segments. A cognate heterologous gen refers to a corresponding gene from another species; thus, if murine APP is the reference, human APP is a cognate heterologous gene (as is porcine, ovine, or rat APP, along with AP genes from other species). A mutated endogenous gene seqeunce can be referred to as a heterologous gene; for example, a transgene encoding a murine APP comprising a Swedish mutation (which is not known in naturally-occurring murine genomes) is a heterologous transgene with respect to murine and non-murine species.

As used herein, the term "targeting construct" refers to a polynucleotide which comprises: (1) at least one homology region having a sequence that is substantially identical to or substantially complementary to a sequence present in a host cell endogenous gene locus, and (2) a targeting region which becomes integrated into an host cell endogenous gene locus by homologous recombination between a targeting construct homology region and said endogenous gene locus sequence. If the targeting construct is a "hit-and-run" or "in-and-out" type construct (Valancius and Smithies (1991) *Mol. Cell. Biol.* 11: 1402; Donehower et al. (1992) *Nature* 356: 215; (1991) *J. NIH Res.* 3: 59; Hasty et al. (1991) *Nature* 350; 243, which are incorporated herein by reference), the targeting region is only transiently incorporated into the endogenous gene locus and is eliminated from the host genome by selection. A targeting region may comprise a sequence that is substantially homologous to an endogenous gene sequence and/or may comprise a nonhomologous sequence, such as a selectable marker (e.g., neo, tk, gpt). The term "targeting construct" does not necessarily indicate that the polynucleotide comprises a gene which becomes integrated into the host genome, nor does it necessarily indicate that the polynucleotide comprises a complete structural gene sequence. As used in the art, the term "targeting construct" is synonymous with the term "targeting transgene" as used herein.

The terms "homology region" and "homology clamp" as used herein refer to a segment (i.e., a portion) of a targeting construct having a sequence that substantially corresponds to, or is substantially complementary to, a predetermined endogenous gene sequence, which can include sequences flanking said gene. A homology region is generally at least about 100 nucleotides long, preferably at least about 250 to 500 nucleotides long, typically at least about 1000 nucleotides long or longer. Although there is no demonstrated theoretical minimum length for a homology clamp to mediate homologous recombination, it is believed that homologous recombination efficiency generally increases with the length of the homology clamp. Similarly, the recombination efficiency increases with the degree of sequence homology between a targeting construct homology region and the endogenous target sequence, with optimal recombination efficiency occurring when a homology clamp is isogenic with the endogenous target sequence. The terms "homology clamp" and "homology region" are interchangeable as used herein, and the alternative terminology is offered for clarity, in view of the inconsistent usage of similar terms in the art. A homology clamp does not necessarily connote formation of a base-paired hybrid structur with an endogenous sequence. Endogenous gene sequences that substantially correspond to, or are substantially complementary to, a transgene homology region are referred to herein as "crossover target sequences" or "endogenous target sequences."

As used herein, the term "minigene" refers to a heterologous gene construct wherein one or more nonessential segments of a gene are deleted with respect to the naturally-occurring gene. Typically, deleted segments are intr nic sequences of at least about 100 basepairs to several kilobases, and may span up to several tens of kilobases or more. Isolation and manipulation of large (i.e., greater than about 50 kilobases) targeting constructs is frequently difficult and may reduce the efficiency of transferring the targeting construct into a host cell. Thus, it is frequently desirable to reduce the size of a targeting construct by deleting one or more nonessential portions of the gene. Typically, intronic sequences that do not encompass essential regulatory elements may be deleted. Frequently, if convenient restriction sites bound a nonessential intr nic sequence of a cloned gene sequence, a deletion of the intronic sequence may be produced by: (1) digesting the cloned DNA with the appropriate restriction enzymes, (2) separating the restriction fragments (e.g., by electrophoresis), (3) isolating the restriction fragments encompassing the essential exons and regulatory elements, and (4) ligating the isolated restriction fragments to form a minigene wherein the exons are in the same linear order as is present in the germline copy of the naturally-occurring gene. Alternate methods for producing a minigene will be apparent to those of skill in the art (e.g., ligation of partial genomic clones which encompass essential exons but which lack portions of intronic sequence). Most typically, the gene segments comprising a minigene will be arranged in the same linear order as is present in the germline gene, however, this will not always be the case. Some desired regulatory elements (e.g., enhancers, silencers) may be relatively position-insensitive, so that the regulatory element will function correctly even if positioned differently in a minigene than in the corresponding germline gene. For example, an enhancer may be located at a different distance from a promoter, in a different orientation, and/or in a different linear order. For example, an enhancer that is located 3' to a promoter in germline configuration might be located 5' to the promoter in a minigene. Similarly, some genes may have exons which are alternatively spliced at the RNA level, and thus a minigene may have fewer exons and/or exons in a different linear order than the corresponding germline gene and still encode a functional gene product. A cDNA encoding a gene product may also be used to construct a minigene. However, since it is often desirable that the heterologous minigene be expressed similarly to the cognate naturally-occurring nonhuman gene, transcription of a cDNA minigene typically is driven by a linked gene promoter and enhancer from the naturally-occurring gene. Frequently, such minigene may comprise a transcriptional regulatory sequence (e.g., promoter and/or enhancer) that confers neuron-specific or CNS-specific transcription of the minigene APP encoding sequences.

As used herein, the term "transcriptional unit" or "transcriptional complex" refers to a polynucleotide sequence that comprises a structural gene (exons), a cis-acting linked promoter and other cis-acting sequences necessary for efficient transcription of the structural sequences, distal regulatory elements necessary for appropriate tissue-specific and developmental transcription of the structural sequences, and additional cis sequences important for efficient transcription and translation (e.g., polyadenylation site, mRNA stability controlling sequences).

As used herein, "linked" means in polynucleotide linkage (i.e., phosphodiester linkage). "Unlinked" means not linked to another polynucleotide sequence; hence, two sequences are unlinked if each sequence has a free 5' terminus and a free 3' terminus.

As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame.

As used herein, the term "correctly targeted construct" refers to a portion of the targeting construct which is integrated within or adjacent to an endogenous crossover targ t sequence, such as a portion of an endogenous APP gene locus. For example but not limitation, a portion of a targeting transg ne encoding neo and flanked by homology regions having substantial identity with endogenous APP gene sequences flanking the first exon, is correctly targeted when said transgene portion is integrated into a chromosomal location so as to replace, for example, the first exon of the endogenous APP gene. In contrast and also for example, if the targeting transgene or a portion thereof is integrated into a nonhomologous region and/or a region not within about 50 kb of a APP gene sequence, the resultant product is an incorrectly targeted transgene. It is possible to generate cells having both a correctly targeted transgene(s) and an incorrectly targeted transgene(s). Cells and animals having a correctly targeted transgene(s) and/or an incorrectly targeted transgene(s) may be identified and resolved by PCR and/or Southern blot analysis of genomic DNA.

As used herein, the term "targeting region" refers to a portion of a targeting construct which becomes integrated into an endogenous chromosomal location following homologous recombination between a homology clamp and an endogenous APP gene sequence. Typically, a targeting region is flanked on each side by a homology clamp, such that a double-crossover recombination between each of the homology clamps and their corresponding endogenous APP gene sequences results in replacement of the portion of the endogenous APP gene locus by the targeting region; in such double-crossover gene replacement targeting constructs the targeting region can be referred to as a "replacement region". However, some targeting constructs may employ only a single homology clamp (e.g., some "hit-and-run"-type vectors, see, Bradley et al. (1992) Bio/Technology 10: 534, incorporated herein by reference).

As used herein, the term "replacement region" refers to a portion of a targeting construct flanked by homology regions. Upon double-crossover homologous recombination between flanking homology regions and their corresponding endogenous APP gene crossover target sequences, the replacement region is integrated into the host cell chromosome between the endogenous crossover target sequences. Replacement regions can be homologous (e.g., have a sequence similar to the endogenous APP gene sequence but having a point mutation or missense mutation), nonhomologous (e.g., a neo gene expression cassette), or a combination of homologous and nonhomologous regions. The replacement region can convert the endogenous APP allele into an APP alelle comprising a Swedish mutation; for example, the replacement region can span the portion of the APP gene encoding residues 595 and 596 of the 695 amino acid long APP isoform (or its nonhuman equivalent) and the replacement region can comprise a sequence encoding aspargine$^{595}$-leucine$^{596}$ at the 595 and 596 positions (acording to the numbering of Kang et al. (1987) op.cit).

The terms "functional disruption" or "functionally disrupted" as used herein means that a gene locus comprises at least one mutation or structural alteration such that the functionally disrupted gene is incapable of directing the efficient expression of functional gene product. For example but not limitation, an endogenous APP gene that has a neo g ne cassette integrated into an exon (e.g., the third exon) of a APP gene, is not capable of encoding a functional protein (isoform) that comprises the inactivated exon, and is therefore a functionally disrupted APP gene Locus. Also for example, a targeted mutation in the exons of an endogenous APP gene may result in a mutated endogenous gene that can express a truncated APP protein isoform. Functional disruption can include th complete substitution of a heterologous APP gene locus in place of an endogenous APP locus, so that, for example, a targeting transgene that replaces the entire mouse APP locus with a human APP Swedish mutation allele, which may be functional in the mouse, is said to have functionally disrupted the endogenous murine APP locus by displacing it. Preferably, at least one exon which is incorporated into the mRNAs encoding most or all of the APP isoforms are functionally disrupted. Deletion or interruption of essential transcriptional regulatory elements, polyadenylation signal(s), splicing site sequences will also yield a functionally disrupted gene. Functional disruption of an endogenous APP gene, may also be produced by other methods (e.g., antisense polynucleotide gene suppression). The term "structurally disrupted" refers to a targeted gene wherein at least one structural (i.e., exon) sequence has been altered by homologous gene targeting (e.g., by insertion, deletion, point mutation(s), and/or rearrangement). Typically, APP alleles that are structurally disrupted are consequently functionally disrupted, however APP alleles may also be functionally disrupted without concomitantly being structurally disrupted, i.e., by targeted alteration of a non-exon sequence such as ablation of a promoter. An allele comprising a targeted alteration that interferes with the efficient expression of a functional gen product from the allele is referred to in the art as a "null allele" or "knockout allele".

The term "agent" is used herein to denote a chemical compound, a mixture of chemical compounds, a biological macromolecule, or an extract made from biological materials such as bacteria, plants, fungi, or animal (particularly mammalian) cells or tissues.

As used herein, "isoform", "APP", and "APP isoform" refer to a polypeptide that is encoded by at least one exon of the APP gene (Kitaguchi et al. (1988) *Nature* 331:530; Ponte et al., ibid., p.525; R. E. Tanzi, ibid., p.528; de Sauvage and Octave (1989) *Science* 245:651; Golde et al. (1990) *Neuron* 4:253). An APP isoform may be encoded by an APP allele (or exon thereof) that is associated with a form of Alzheimer's disease or that is not associated with an AD disease phenotype.

The term "β-amyloid gene" is used herein as a synonym for the APP gene, as β-amyloid is a protein product produced by a post-translational cleavage of an APP gene product.

As used herein, "APP$^{695}$", "APP$^{751}$", and "APP$^{770}$" refer, respectively, to the 695, 751, and 770 amino acid residue long polypeptides encoded by the human APP gene (Ponte et al. *loc. cit.;* Kitaguchi et al. *loc. cit.;* Tanzi et al. *loc. cit.*).

As used herein, "codon 595" and "codon 596" refer to the codons (i.e., the trinucleotide sequences) that encodes the 595th and 596th amino acid positions in APP$^{695}$, or the amino acid position in an APP isoform or fragment that corresponds to the 595th and 596th positions in APP$^{695}$ according to the numbering convnetion in kang et al. (1987) *op. cit*). For example but not limitation, a 600 residue long fragment that is produced by truncating APP$^{695}$ by removing the 95 N-terminal amino acids has its 500th and 501st amino acid positions corresponding to codons 595 and 596 of APP$^{695}$. In fact, as used herein, the Swedish mutation is characterized by asparagine and leucine residues, respectively, at amino acid positions 595 and 596 in APP$^{695}$ which correspond to amino acid positions 670 and 671 in APP$^{770}$.

DETAILED DESCRIPTION

Generally, the nomenclature used hereafter and the laboratory procedures in cell culture, molecular genetics, and nucleic acid chemistry and hybridization described below are those well known and commonly employed in the art. Standard techniques are used for recombinant nucleic acid methods, polynucleotide synthesis, cell culture, and transgene incorporation (e.g., electroporation, microinjection, lipofection). Generally enzymatic reactions, oligonucleotide synthesis, and purification steps are performed according to the manufacturer's specifications. The techniques and procedures are generally performed according to conventional methods in the art and various general references which are provided throughout this document. The procedures therein are believed to be well known in the art and are provided for the convenience of the reader. All the information contained therein is incorporated herein by reference.

Chimeric targeted mice are derived according to Hogan, et al., *Manipulating the Mouse Embryo: A Laboratory Manual,* Cold Spring Harbor Laboratory (1988) and *Teratocarcinomas and Embryonic Stem Cells: A Practical Approach,* E. J. Robertson, ed., IRL Press, Washington, D.C., (1987) which are incorporated herein by reference.

Embryonic stem cells are manipulated according to published procedures (*Teratocarcinomas and Embryonic Stem Cells: A Practical Approach,* E. J. Robertson, ed., IRL Press, Washington, D.C. (1987); Zjilstra et al., *Nature* 342:435–438 (1989); and Schwartzberg et al., *Science* 246: 799–803 (1989), each of which is incorporated herein by reference).

Oligonucleotides can be synthesized on an Applied Bio Systems oligonucleotide synthesizer according to specifications provided by the manufacturer.

In general, the invention encompasses methods and polynucleotide constructs which are employed for generating nonhuman transgenic animals expressing an APP polypeptide comprising the Swedish mutation. In some embodiments, the nonhuman transgenic animals expressing a Swedish mutation APP also have the endogenous APP gene locus functionally disrupted. Advantageously, the Swedish mutation results in enhanced expression of Aβ, with animals or cells generally expressing transgene-encoded Swedish mutation Aβ at a significantly higher. level than normal Aβ. It is believed that the Met$^{596}$ to Leu$^{596}$ is of particular importance in the preferential expression of the Swedish Aβ as compared to the normal (wildtype) Aβ.

Newly identified secreted fragments comprise the amino-terminal portion of βAPP (Aβ) which remains after cleavage and will be referred to hereinafter as the amino-terminal fragm nt form of βAPP (ATF-βAPP). ATF-βAPP is believed to be the product of an alternative secretory processing pathway for Aβ, which pathway is present even in normal (non-diseased) cells. It is further believed, however, that the alternate secretory pathway may be responsible for an essential event in the production of Aβ in diseased cells in patients, and that abnormal production of ATF-βAPP may be involved in diseases related to Aβ plaque, particularly Alzheimer's disease and Down's syndrome.

Particularly preferred animal models for β-secretase cleavage of Aβ are transgenic animals which express the Swedish mutation of the Aβ gene, as described above. It has been found that such transgenic animals, particularly transgenic mice, produce high quantities of ATF-βAPP which may detected according to the methods of the present invention. In particular, it has been found that Swedish mutation of Aβ produces quantities of the ATF-βAPP which will usually be at least two-fold higher than wild type human βAPP expressed in animals. Usually, production will be significantly higher, typically being at least two-fold higher. With such elevated levels of ATF-βAPP production, monitoring β-secretase activity under different conditions is greatly facilitated. In particular, screening for drugs and other therapies for inhibiting β-secretase activity (and thus inhibiting βAPP production) are greatly simplified in animals models expressing the Swedish mutation of human βAPP.

Agents are administered to test animals, such as test mice, which are transgenic and which express the Swedish mutation of human βAPP. Particular techniques for producing transgenic mice which express the Swedish form of βAPP are described hereinafter. It will be appreciated that the preparation of other transgenic animals expressing the Swedish human βAPP may easily be accomplished, including rats, hamsters, guinea pigs, rabbits, and the like. The effect of test compounds on ATF-βAPP production in test animals may be measured in various specimens from the test animals.

The effect of test agents on ATF-βAPP production in test animals may be measured in various specimens from the test animals. In all cases, it will be necessary to obtain a control value which is characteristic of the level of ATF-βAPP production in the test animal in the absence of test compound(s). In cases where the animal is sacrificed, it will be necessary to base such control values on an average or a typical value from other test animals which have been transgenically modified to express the Swedish mutant of human βAPP but which have not received the administration of any test compounds or any other substances expected to affect the level of production of ATF-βAPP. Once such control level is determined, test compounds can b administered to additional test animals, where deviation from the average control value indicates that the test compound had an effect on the β-secretase activity in the animal. Test substances which are considered positive, i.e., likely to be beneficial in the treatment of Alzheimer's disease or other β-amyloid-related conditions, will be those which are able to reduce the level of ATF-βAPP production, preferably by at least 20%, more preferably by at least 50%, and most preferably by at least 80%.

The test agents can be any molecule, compound, or oth r substance which can be added to the cell culture or administered to the test animal without substantially interfering with cell or animal viability. Suitable test agents may be small molecules, biological polymers, such as polypeptides, polysaccharides, polynucleotides, and the like. The test compounds will typically be administered to transgenic animals at a dosage of from 1 ng/kg to 10 mg/kg, usually from 10 μg/kg to 1 mg/kg.

Test compounds which are able to inhibit secretion or animal production of ATF-βAPP are considered as candidates for further determinations of the ability to block β-amyloid production in animals and humans. Inhibition of secretion or Production indicates that cleavage of βAPP at the amino-terminus of βAP has likely been at least partly blocked, reducing the amount of a processing intermediate available for conversion to β-amyloid peptide.

The present invention further comprises pharmaceutical compositions incorporating a compound selected by the above-described method and including in a pharmaceutically acceptable carrier. Such pharmaceutical compositions should contain a therapeutic or prophylactic amount of at least one compound identified by the method of the present invention. The pharmaceutically acceptable carrier can be any compatible, non-toxic substance suitable to deliver the compounds to an intended host. Sterile water, alcohol, fats, waxes, and inert solids may be used as the carrier. Pharmaceutically acceptable adjuvants, buffering agents, dispersing agents, and the like may also be incorporated into the pharmaceutical compositions. Preparation of pharmaceutical conditions incorporating active agents is well described in the medical and scientific literature. See, for example, Remington's Pharmaceutical Sciences, Mack Publishing Company, Easton, Pa., 16th Ed., 1982, the disclosure of which is incorporated herein by reference.

The pharmaceutical compositions just described are suitable for systemic administration to the host, including both parenteral, topical, and oral administration. The pharmaceutical compositions may be administered parenterally, i.e. subcutaneously, intramuscularly, or intravenously. Thus, the present invention provides compositions for administration to a host, where the compositions comprise a pharmaceutically acceptable solution of the identified compound in an acceptable carrier, as described above.

Transgenes Encoding Heterologous Swedish Mutation APP Protein

In a preferred embodiment of the invention, a transgene encoding a heterologous APP protein comprising the Swedish mutation (asparagine$^{595}$-leucine$^{596}$) is transferred into a fertilized embryo or an ES cell to produce a transgenic nonhuman animal that expresses APP polypeptide(s) comprising the Swedish mutation. A transgene encoding a heterologous Swedish mutation APP protein comprises structural sequences encoding a heterologous Swedish mutation APP protein, and generally also comprises linked regulatory elements that drive expression of the heterologous Swedish mutation APP protein in the nonhuman host. However, endogenous regulatory elements in the genome of the nonhuman host may be exploited by integrating the transgene sequences into a chromosomal location containing functional endogenous regulatory elements which are suitable for the expression of the heterologous structural sequences. Such targeted integration is usually performed by homologous gene targeting as described supra, wherein the heterologous transgene would comprise at least one homology clamp.

When a heterologous transgene relies on its own regulatory elements, suitable transcription elements and polyadenylation sequence(s) are included. At least one promoter is linked upstream of the first structural sequence in an orientation to drive transcription of the heterologous structural sequences. Sometimes the promoter from the naturally-occurring heterologous gene is used (e.g., a human APP promoter is used to drive expression of a human Swedish mutation APP transgene). Alternatively, the promoter from the endogenous cognate APP gene may be used (e.g., the murine APP promoter is used to drive expression of a human Swedish mutation APP transgene). Alternatively, a transcriptional regulatory element heterogenous with respect to both the transgene encoding sequences and the nonhuman host animal can be used (e.g., a rat promoter and/or enhancer operably linked to a nucleotide sequence encoding human Swedish mutation APP, wherein the transgene is introduced into mice).

In some embodiments, it is preferable that the transgene sequences encoding the Swedish mutation APP polypeptide are under the transcriptional control of promoters and/or enhancers (and/or silencers) which are not operably linked in naturally-occurring APP genes (i.e., non-APP promoters and/or enhancers). For example, some embodiments will employ transcriptional regulatory sequences which confer high level expression and/or in a cell type-specific expression pattern (e.g., a neuron-specific Promoter). The rat neural-specific enolase (NSE) promoter (Forss-Petter (1990) *Neuron* 5; 187) is a preferred transcriptional regulatory element for operable linkage to a nucleotide sequence encoding a Swedish mutation APP polypeptide. Other promoters and/or enhancers which confer efficient expression to the transgene-encoded APP sequence in brain tissue generally are preferred.

Various promoters having different strengths (e.g., pgk, tk, dhfr) may be substituted in the discretion of the practitioner, however it is essential that the promoter function in the nonhuman host and it is desirable in some embodiments that the promoter drive expression in a developmental pattern or cell type-specific pattern (and at expression levels) similar to a naturally-occurring APP gene in a parallel host animal lacking the transgene.

A heterologous transgene generally encodes at least one full-length APP isoform (e.g., a 695aa isoform). The heterologous transgene may comprise a polynucleotide spanning the entire genomic APP gene or portion thereof, may comprise a minigene, may comprise a single contiguous coding segment (e.g., cDNA), or may comprise a combination thereof. Frequently, the transgene encodes a human APP polypeptide sequence comprising the Swedish mutation, however transgenes encoding nonhuman APP polypeptides comprising the Swedish mutation may also be used. Generally, the transgene will encode a full-length naturally-occurring APP isoform (e.g., APP$^{695}$, APP$^{751}$, or APP$^{770}$) further comprising the Swedish mutation.

The transgenes encoding APP polypeptides comprising the Swedish mutation will frequently will also comprise one or more linked selectable marker (infra).

Transgenes encoding heterologous APP polypeptides comprising -he Swedish mutation molecules may be transferred into the nonhuman host genome in several ways. A heterologous transgene may be targeted to a specific predetermined chromosomal location by homologous targeting, as described supra for gene targeting. Heterologous transgenes may be transferred into a host genome in pieces, by sequential homologous targeting, to reconstitute a complete heterologous gene in an endogenous host chromosomal location. In contradistinction, a heterologous transgene may be randomly integrated separately from or without using a APP gene targeting construct. A heterologous transgene may be co-transferred with an APP gene targeting construct and, if desired, selected for with a separate, distinguishable selectable marker and/or screened with PCR or Southern blot analysis of selected cells. Alternatively, a heterologous transgene may be introduced into ES cells prior to or subsequent to introduction of a APP gene targeting construct and selection therefor. Most conveniently, a heterologous transgene is introduced into the germline of a nonhuman animal by nonhomologous transgene integration via pronuclear injection, and resultant transgenic lines are bred into a homozygous knockout background having functionally disrupted cognate endogenous APP gene. Homozygous knockout mice can also be bred and the heterologous Swedish mutation APP transgene introduced into embryos of knockout mice directly by standard pronuclear injection or other means known in the art.

Gene Targeting

In some embodiments, the endogenous nonhuman APP alleles are functionally disrupted so that expression of endogenously encoded APP is suppressed or eliminated, so as to not interfere or contaminate transgene-encoded APP comprising the Swedish mutation. In one variation, an endogenous APP allele is converted to comprise the Swedish mutation by homologous gene targeting.

Gene targeting, which is a method of using homologous recombination to modify a mammalian genome, can be used to introduce changes into cultured cells. By targeting a gene of interest in embryonic stem (ES) cells, these changes can be introduced into the germlines of laboratory animals to study the effects of the modifications on whole organisms, among other uses. The gene targeting procedure is accomplished by introducing into tissue culture cells a DNA targeting construct that has a segment homologous to a target locus and which also comprises an intended sequence modification (e.g., insertion, deletion, point mutation). The treated cells are then screened for accurate targeting to identify and isolate those which have been properly targeted. A common scheme to disrupt gene function by gene targeting in ES cells is to construct a targeting construct which is designed to undergo a homologous recombination with its chromosomal counterpart in the ES cell genome. Th targeting constructs are typically arranged so that they insert additional sequences, such as a positive selection marker, into coding elements of the target gene, thereby functionally disrupting it. Targeting constructs usually are insertion-type or replacement-type constructs (Hasty et al. (1991) *Mol. Cell. Biol.* 11: 4509).

Targeting of the Endogenous APP Gene

The invention encompasses methods to produce nonhuman animals (e.g., non-primate mammals) that have the endogenous APP gene inactivated by gene targeting with a homologous recombination targeting construct. Typically, a nonhuman APP gene sequence is used as a basis for producing PCR primers that flank a region that will be used as a homology clamp in a targeting construct. The PCR primers are then used to amplify, by high fidelity PCR amplification (Mattila et al. (1991) *Nucleic Acids Res.* 19: 4967; Eckert, K. A. and Kunkel, T. A. (1991) *PCR Methods and Applications* 1: 17; U.S. Pat. No. 4,683,202, which are incorporated herein by reference), a genomic sequence from a genomic clone library or from a preparation of genomic DNA, preferably from the strain of nonhuman animal that is to be targeted with the targeting construct. The amplified DNA is then used as a homology clamp and/or targeting region. Thus, homology clamps for targeting a nonhuman APP gene may be readily produced on the basis of nucleotide sequence information available in the art and/or by routine cloning. General principles regarding the construction of targeting constructs and selection methods are reviewed in Bradley et al. (1992) *Bio/Technology* 10: 534, incorporated herein by reference.

Endogenous nonhuman APP genes may be functionally disrupted and, optionally, may be replaced by transgenes encoding APP comprising the Swedish mutation.

Targeting constructs can be transferred into pluripotent stem cells, such as murine embryonal stem cells, wherein the targeting constructs homologously recombine with a portion of an endogenous APP gene locus and create mutation(s) (i.e., insertions, deletions, rearrangements, sequence replacements, and/or point mutations) which prevent the functional expression of the endogenous APP gene.

A preferred method of the invention is to delete, by targeted homologous recombination, essential structural elements of the endogenous APP gene. For example, a targeting construct can homologously recombine with an endogenous APP gene and delete a portion spanning substantially all of one or more of the exons to create an exon-depleted allele, typically by inserting a replacement region lacking the corresponding exon(s). Transgenic animals homozygous for the exon-depleted allele (e.g., by breeding of heterozygotes to each other) produce cells which are essentially incapable of expressing a functional endogenous APP polypeptide (preferably incapable of expressing any of the naturally-occurring isoforms). Similarly, homologous gene targeting can be used, if desired, to functionally disrupt an APP gene by deleting only a portion of an exon.

Targeting constructs can also be used to delete essential regulatory elements of an endogenous APP gene, such as promoters, enhancers, splice sites, polyadenylation sites, and other regulatory sequences, including cis-acting sequences that occur upstream or downstream of the APP structural gene but which participate in endogenous APP gene expression. Deletion of regulatory elements is typically accomplished by inserting, by homologous double-crossover recombination, a replacement region lacking the corresponding regulatory element(s).

A alternative preferred method of the invention is to interrupt essential structural and/or regulatory elements of an endogenous APP gene by targeted insertion of a polynucleotide sequence, and thereby functionally disrupt the endogenous APP gene. For example, a targeting construct can homologously recombine with an endogenous APP gene and insert a nonhomologous sequence, such as a neo expression cassette, into a structural element (e.g., an exon) and/or regulatory element (e.g., enhancer, promoter, splice site, polyadenylation site) to yield a targeted APP allele having an insertional interruption. The inserted sequence can range in size from about 1 nucleotide (e.g., to produce a frameshift in an exon sequence) to several kilobases or more, as limited by efficiency of homologous gene targeting with targeting constructs having a long nonhomologous replacement region.

Targeting constructs of the invention can also be employed to replace a portion of an endogenous APP gene with an exogenous sequence (i.e., a portion of a targeting transgene); for example, the first exon of an APP gene may be replaced with a substantially identical portion that contains a nonsense or missense mutation.

Inactivation of an endogenous mouse APP locus is achieved by targeted disruption of the appropriate gene by homologous recombination in mouse embryonic stem cells. For inactivation, any targeting construct that produces a genetic alteration in the target APP gene locus resulting in the prevention of effective expression of a functional gene product of that locus may be employed. If only regulatory elements are targeted, some low-level expression of the targeted gene may occur (i.e., the targeted allele is "leaky"), however the level of expression may be sufficiently low that the leaky target d allele is functionally disrupted.

Generation of Null APP Alleles and Knockout Mice

In one embodiment of the invention, an endogenous APP gene in a nonhuman host is functionally disrupted by homologous recombination with a targeting construct that does not comprise a cognate heterologous APP gene segment comprising the Swedish mutation. In this embodiment, a portion of the targeting construct integrates into an essential structural or regulatory element of the endogenous APP gene locus, thereby functionally disrupting it to generate a null allele. Typically, null alleles are produced by integrating a nonhomologous sequence encoding a selectable marker (e.g., a neo gene expression cassette) into an essential structural and/or regulatory sequence of an APP gene by homologous recombination of the targeting construct homology clamps with endogenous APP gene sequences, although other strategies (see, infra) may be employed.

Most usually, a targeting construct is transferred by electroporation or microinjection into a totipotent embryonal stem (ES) cell line, such as the murine AB-1 or CCE lines. The targeting construct homologously recombines with endogenous sequences in or flanking an APP gene locus and functionally disrupts at least one allele of the APP gene. Typically, homologous recombination of the targeting construct with endogenous APP locus sequences results in integration of a nonhomologous sequence encoding and expressing a selectable marker, such as neo, usually in the form of a positive selection cassette (infra). The functionally disrupted allele is termed an APP null allele. ES cells having at least one APP null allel are selected for by propagating the cells in a medium that permits the preferential propagation of cells expressing the selectable marker. Selected ES cells are examined by PCR analysis and/or Southern blot analysis to verify the presence of a correctly targeted APP allele. Breeding of nonhuman animals which are heterozygous for a null allele may be performed to produce nonhuman animals homozygous for said null allele, so-called "knockout" animals (Donehower et al. (1992) Nature 256: 215; Science 256: 1392, incorporated herein by reference). Alternatively, ES cells homozygous for a null allele having an integrated selectable marker can be produced in culture by selection in a medium containing high levels of the selection agent (e.g., G418 or hygromycin). Heterozygosity and/or homozygosity for a correctly targeted null allele can be verified with PCR analysis and/or Southern blot analysis of DNA isolated from an aliquot of a selected ES cell clone and/or from tail biopsies.

If desired, a transgene encoding a heterologous APP polypeptide comprising the Swedish mutation can be transferred into a nonhuman host having an APP null allele, preferably into a nonhuman ES cell that is homozygous for the APP null allele. It is generally advantageous that the transgene comprises a promoter and enhancer which drive expression of structural sequences encoding a functional heterologous Swedish mutation APP gene product. Thus, for example and not limitation, a knockout mouse homozygous for null alleles at the APP locus is preferably a host for a transgene which encodes and expresses a functional human APP protein comprising the Swedish mutation. Swedish mutation APP transgenes comprise heterologous APP structural sequences encoding APP polypeptides comprisng the Swedish mutation, either in the form of exons having splice junction sequences, as a contiguous coding segment (e.g., a cDNA), or as a combination of these. Most usually, Swedish mutation APP transgenes encode full-length APP polypeptides, although transgenes can encode truncated APP isoforms, chimeric APP polypeptides (e.g., part human/part mouse), and/or amino-substituted APP variants (i.e., muteins) further comprisng the Swedisn mutation. Typically, transgenes also comprise regulatory elements, such as a promoter and, for optimal expression, an enhancer.

Homologous APP Gene Replacement

In an alternative variation of the invention, an endogenous APP gene in a nonhuman host is functionally disrupted by homologous integration of a cognate heterologous APP gene comprising the Swedish mutation, such that the cognate heterologous APP gene substantially replaces the endogenous APP gene, at least spanning the amino acid 595–596 positions according to the Kang et al. (1987) op.cit numbering convention, and preferably completely replaces the coding sequences of the endogenous APP gene. Preferably, the heterlogous Swedish mutation APP gene is linked, as a consequence of homologous integration, to regulatory sequences (e.g., an enhancer) of the endogenous APP gene so that the heterologous Swedish mutation gene is expressed under the transcriptional control of regulatory elements from the endogenous APP gene locus. Nonhuman hosts which are homozygous for such replacement alleles (i.e., a host chromosomal APP locus which encodes a cognate heterologous Swedish mutation APP gene product) may be produced according to methods described herein. Such homozygous nonhuman hosts generally will express a heterologous Swedish mutation APP protein but do not express the endogenous APP protein. Most usually, the expression pattern of the heterologous Swedish mutation APP gene will substantially mimic the expression pattern of the endogenous APP gene in the naturally-occurring (non-transgenic) nonhuman host. For example but not limitation, a transgenic mouse having human Swedish mutation APP gene sequences replacing the endogenous murine APP gene sequences and which are transcriptionally controlled by endogenous murine regulatory sequences generally will be expressed similarly to the murine APP in naturally occurring non-transgenic mice.

Generally, a replacement-type targeting construct is employed for homologous gene replacement. Double-crossover homologous recombination between endogenous APP gene sequences and homology clamps flanking the replacement region (i.e., the heterologous Swdish mutation APP encoding region) of the targeting construct result in targeted integration of the heterologous Swedish mutation APP gene segments. Usually, the homology clamps of the transgene comprise sequences which flank the endogenous APP gene segments, so that homologous recombination results in concomitant deletion of the endogenous APP gene segments and homologous integration of the heterologous gene segments. Substantially an entire endogenous APP gene may be replaced with a heterologous APP gene comprising the Swedish mutation by a single targeting event or by multiple targeting events (e.g., sequential replacement of individual exons). One or more selectable markers, usually in the form of positive or negative selection expression cassettes, may be positioned in the targeting construct replacement region; it is usually preferred that selectable markers are located in intron regions of the heterologous replacement region.

ES cells harboring a heterologous Swedish mutation APP gene, such as a replacement allele, may be selected in several ways. First, a selectable marker (e.g., neo, gpt, tk) may be linked to the heterologous Swedish mutation APP gene (e.g., in an intron or flanking sequence) in the targeting construct so that cells having a replacement allele may be selected for. Most usually, a heterologous APP gene targeting construct will comprise both a positive selection expression cassette and a negative selection expression cassette, so that homologously targeted cells can be selected for with a positive-negative selection scheme (Mansour et al. (1988) op.cit., incorporated herein by reference). Generally, a positive selection expression cassette is positioned in an intron region of the heterologous Swedish mutation APP gene replacement region, while a negative selection expression cassette is positioned distal to a homology clamp, such that double-crossover homologous recombination will result in the integration of the positive selection cassette and the loss of the negative selection cassette.

Targeting Constructs

Several gene targeting techniques have been described, including but not limited to: co-electroporation, "hit-and-run", single-crossover integration, and double-crossover recombination (Bradley et al. (1992) *Bio/Technology* 10:534). The invention can be practiced using essentially any applicable homologous gene targeting strategy known in the art. The configuration of a targeting construct depends upon the specific targeting technique chosen. For example, a targeting construct for single-crossover integration or "hit-and-run" targeting need only have a single homology clamp linked to the targeting region, whereas a double-crossover replacement-type targeting construct requires two homology clamps, one flanking each side of the replacement region.

For example and not limitation, a preferred embodiment is a targeting construct comprising, in order: (1) a first homology clamp having a sequence substantially identical to a sequence within about 3 kilobases upstream (i.e., in the direction opposite to the translational reading frame of the exons) of an exon of an endogenous APP gene, (2) a replacement region comprising a positive selection cassette having a pgk promoter driving transcription of a neo gene, (3) a second homology clamp having a sequence substantially identical to a sequence within about 3 kilobases downstream of said exon of said endogenous APP gene, and (4) a negative selection cassette, comprising a HSV tk promoter driving transcription of an HSV tk gene. Such a targeting construct is suitable for double-crossover replacement recombination which deletes a portion of the endogenous APP locus spanning said exon and replaces it with the replacement region having the positive selection cassette. If the deleted exon is essential for expression of a functional APP gene product, the resultant exon-depleted allele is functionally disrupted and is termed a null allele.

Targeting constructs of the invention comprise at least one APP homology clamp linked in polynucleotide linkage. (i.e., by phosphodiester bonds) to a targeting region. A homology clamp has a sequence which substantially corresponds to, or is substantially complementary to, an endogenous APP gene sequence of a nonhuman host animal, and may comprise sequences flanking the APP gene.

Although no lower or upper size boundaries for recombinogenic homology clamps for gene targeting have been conclusively determined in the art, the best mode for homology clamps is believed to be in the range between about 50 basepairs and several tens of kilobases. Consequently, targeting constructs are generally at least about 50 to 100 nucleotides long, preferably at least about 250 to 500 nucleotides long, more preferably at least about 1000 to 2000 nucleotides long, or longer. Construct homology regions (homology clamps) are generally at least about 50 to 100 bases long, preferably at least about 100 to 500 bases long, and more preferably at least about 750 to 2000 bases long. It is believed that homology regions of about 7 to 8 kilobases in length are preferred, with one preferred embodiment having a first homology region of about 7 kilobases flanking one side of a replacement region and a second homology region of about 1 kilobase flanking the other side of said replacement region. The length of homology (i.e., substantial identity) for a homology region may be selected at the discretion of the practitioner on the basis of the sequence composition and complexity of the endogenous APP gene target sequence(s) and guidance provided in the art (Hasty et al. (1991) *Mol. Cell. Biol.* 11: 5586; Shulman et al. (1990) *Mol. Cell. Biol.* 10: 4466). Targeting constructs have at least one homology region having a sequence that substantially corresponds to, or is substantially complementary to, an endogenous APP gene sequence (e.g., an exon sequence, an enhancer, a promoter, an intronic sequence, or a flanking sequence within about 3–20 kb of a APP gene). Such a targeting transgene homology region serves as a template for homologous pairing and recombination with substantially identical endogenous APP gene sequence(s). In targeting constructs, such homology regions typically flank the replacement region, which is a region of the targeting construct that is to undergo replacement with the targeted endogenous APP gene sequence (Berinstein et al. (1992) *Mol. Cell. Biol.* 12: 360). Thus, a segment of the targeting construct flanked by homology regions can replace a segment of an endogenous APP gene sequence by double-crossover homologous recombination. Homology regions and targeting regions are linked together in conventional linear polynucleotide linkage (5' to 3' phosphodiester backbone). Targeting constructs are generally double-stranded DNA molecules, most usually linear.

Without wishing to be bound by any particular theory of homologous recombination or gene conversion, it is believed that in such a double-crossover replacement recombination, a first homologous recombination (e.g., strand exchange, strand pairing, strand scission, strand ligation) between a first targeting construct homology region and a first endogenous APP gene sequence is accompanied by a second homologous recombination between a second targeting construct homology region and a second endogenous APP gene sequence, thereby resulting in the portion of the targeting construct that was located between the two homology regions replacing the portion of the endogenous APP gene that was located between the first and second endogenous APP gene sequences. For this reason, homology regions are generally used in the same orientation (i.e., the upstream direction is the same for each homology region of a transgene to avoid rearrangements). Double-crossover replacement recombination thus can be used to delete a portion of an endogenous APP gene and concomitantly transfer a nonhomologous portion (e.g., a neo gene expression cassette) into the corresponding chromosomal location. Double-crossover recombination can also be used to add a nonhomologous portion into an endogenous APP gene without deleting endogenous chromosomal portions. However, double-crossover recombination can also be employed simply to delete a portion of an endogenous APP gene sequence without transferring a nonhomologous portion into the endogenous APP gene (see Jasin et al. (1988) *Genes Devel.* 2:1353). Upstream and/or downstream from the nonhomologous portion may be a gene which provides for identification of whether a double-crossover homologous recombination has occurred; such a gene is typically the HSV tk gene which may be used for negative selection.

Typically, targeting constructs of the invention are used for functionally disrupting endogenous APP genes and comprise at least two homology regions separated by a nonhomologous sequence which contains an expression cassette encoding a selectable marker, such as neo (Smith and Berg (1984) *Cold Spring Harbor Symp. Quant. Biol.* 49: 171; Sedivy and Sharp (1989) *Proc. Natl. Acad. Sci. (U.S.A.)* 86: 227; Thomas and Capecchi (1987) op.cit.). However, some targeting transgenes of the invention may have the homology region(s) flanking only one side of a nonhomologous sequence. Targeting transgenes of the invention may also be of the type referred to in the art as "hit-and-run" or "in-and-out" transgenes (Valancius and Smithies (1991) *Mol. Cell. Biol.* 11: 1402; Donehower et al. (1992) *Nature* 356: 215; (1991) *J. NIH Res.* 3: 59; which are incorporated herein by reference).

The positive selection expression cassette encodes a selectable marker which affords a means for selecting cells which have integrated targeting transgene sequences spanning the positive selection expression cassette. The negative selection expression cassette encodes a selectable marker which affords a means for selecting cells which do not have an integrated copy of the negative selection expression cassette. Thus, by a combination positive-negative selection protocol, it is possible to select cells that have undergone homologous replacement recombination and incorporated the portion of the transgene between the homology regions (i.e., the replacement region) into a chromosomal location by selecting for the presence of the positive marker and for the absence of the negative marker.

Preferred expression cassettes for inclusion in the targeting constructs of the invention encode and express a selectable drug resistance marker and/or a HSV thymidine kinase enzyme. Suitable drug resistance genes include, for example: gpt (xanthine-guanine phosphoribosyltransferase), which can be selected for with mycophenolic acid; neo (neomycin phosphotransferase), which can be selected for with G418 or hygromycin; and DFHR (dihydrofolate reductase), which can be selected for with methotrexate (Mulligan and Berg (1981) *Proc. Natl. Acad. Sci.* (*U.S.A.*) 78: 2072; Southern and Berg (1982) *J. Mol. Appl. Genet.* 1: 327; which are incorporated herein by reference).

Selection for correctly targeted recombinants will generally employ at least positive selection, wherein a nonhomologous expression cassette encodes and expresses a functional protein (e.g., neo or gpt) that confers a selectable phenotype to targeted cells harboring the endogenously integrated expression cassette, so that, by addition of a selection agent (e.g., G418 or mycophenolic acid) such targeted cells have a growth or survival advantage over cells which do not have an integrated expression cassette.

It is preferable that selection for correctly targeted homologous recombinants also employ negative selection, so that cells bearing only nonhomologous integration of the transgene are selected against. Typically, such negative selection employs an expression cassette encoding the herpes simplex virus thymidine kinase gene (HSV tk) positioned in the transgene so that it should integrate only by nonhomologous recombination. Such positioning generally is accomplished by linking the HSV tk expression cassette (or other negative selection cassette) distal to the recombinogenic homology regions so that double-crossover replacement recombination of the homology regions transfers the positive selection expression cassette to a chromosomal location but does not transfer the HSV tk gene (or other negative selection cassette) to a chromosomal location. A nucleoside analog, gancyclovir, which is preferentially toxic to cells expressing HSV tk, can be used as the negative selection agent, as it selects for cells which do not have an integrated HSV tk expression cassette. FIAU may also be used as a selective agent to select for cells lacking HSV tk.

In order to reduce the background of cells having incorrectly integrated targeting construct sequences, a combination positive-negative selection scheme is typically used (Mansour et al. (1988). op.cit., incorporated herein by reference).

Generally, targeting constructs of the invention preferably include: (1) a positive selection expression cassette flanked by two homology regions that are substantially identical to host cell endogenous APP gene sequences, and (2) a distal negative selection expression cassette. However, targeting constructs which include only a positive selection expression cassette can also be used. Typically, a targeting construct will contain a positive selection expression cassette which includes a neo gene linked downstream (i.e., towards the carboxy-terminus of the encoded polypeptide in translational reading frame orientation) of a promoter such as the HSV tk promoter or the pgk promoter. More typically, the targeting transgene will also contain a negative selection expression cassette which includes an HSV tk gene linked downstream of a HSV tk promoter.

It is preferred that targeting constructs of the invention have homology regions that are highly homologous to the predetermined target endogenous DNA sequence(s), preferably isogenic (i.e., identical sequence). Isogenic or nearly isogenic sequences may be obtained by genomic cloning or high-fidelity PCR amplification of genomic DNA from the strain of nonhuman animals which are the source of the ES cells used in the gene targeting procedure.

To disrupt the murine APP gene, a targeting construct based on the design employed by Jaenisch and co-workers (Zjilstra, et al. (1989) op.cit.) for the successful disruption of the mouse β2-microglobulin gene can be used. The neomycin resistance gene (neo), from the plasmid pMC1NEO is inserted into the coding region of the target APP gene. The pMC1NEO insert uses a hybrid viral promoter/enhancer sequence to drive neo expression. This promoter is active in embryonic stem cells. Therefore, neo can be used as a selectable marker for integration of the knock-out construct. The HSV thymidine kinase (tk) gene is added to the end of the construct as a negative selection marker against random insertion events (Zjilstra, et al., op.cit.).

Vectors containing a targeting construct are typically grown in *E. coli* and then isolated using standard molecular biology methods, or may be synthesized as oligonucleotides. Direct targeted inactivation which does not require prokaryotic or eukaryotic vectors may also be done. Targeting transgenes can be transferred to host cells by any suitable technique, including microinjection, electroporation, lipofection, biolistics, calcium phosphate precipitation, and viral-based vectors, among oth rs. Other methods used to transform mammalian cells include the use of Polybrene, protoplast fusion, and others (see, generally, Sambrook et al. Molecular Cloning: A Laboratory Manual, 2d ed., 1989, Cold Spring Harbor Laboratory Press, Cold Spring Harb r, N.Y., which is incorporated herein by reference).

For making transgenic non-human animals (which include homologously targeted non-human animals), embryonal stem cells (ES cells) are preferred. Murine ES cells, such as AB-1 lin grown on mitotically inactive SNL76/7 cell feeder layers (McMahon and Bradley (1990) Cell 62: 1073) essentially as described (Robertson, E. J. (1987) in Teratocarcinomas and Embryonic Stem Cells: A Practical Approach. E. J. Robertson, ed. (oxford: IRL Press), p. 71–112) may be used for homologous gene targeting. Other suitable ES lines include, but are not limited to, the E14 line (Hooper et al. (1987) Nature 326: 292–295), the D3 line (Doetschman et al. (1985) J. Embryol. Exp. Morph. 87: 27–45), and the CCE line (Robertson et al. (1986) Nature 323: 445–448). The success of generating a mouse line from ES cells bearing a specific targeted mutation depends on the pluripotence of the ES cells (i.e., their ability, once injected into a host blastocyst, to participate in embryogenesis and contribute to the germ cells of the resulting animal). The blastocysts containing the injected ES cells are allowed to develop in the uteri of pseudopregnant nonhuman females and are born as chimeric mice. The resultant transgenic mice are chimeric for cells having inactivated endogenous APP loci and are backcrossed and screened for the presence of the correctly targeted transgene(s) by PCR or Southern blot analysis on tail biopsy DNA of offspring so as to identify transgenic mice heterozygous for the inactivated APP locus. By performing the appropriate crosses, it is possible to produce a transgenic nonhuman animal homozygous for functionally disrupted APP aleles, and optionally also harboring a transgene encoding a heterologous APP polypeptide comprising the Swedish mutation. Such transgenic animals are substantially incapable of making an endogenous APP gene product but express the Swedish mutation heterologous APP.

Commercial Research and Screening Uses

Nonhuman animals comprising transgenes which encode Swedish mutation APP (and thus Swedish mutation Aβ), can be used commercially to screen for agents having the effect of lowering Aβ production and/or accumulation. Such agents can be developed as pharmaceuticals for treating abnormal APP processing and/or Alzheimer's disease, amongst other neurodegenerative conditions. For example, the p53 knockout mice of Donehower et al. (1992) Nature 356: 215 have found wide acceptance as commercial products for carcinogen screening and the like. The transgenic animals of the present invention exhibit abnormal APP processing and expression, and can be used for pharmaceutical screening and as disease models for neurodegenerative diseases and APP biochemistry. Such animals have many uses, including but not limited to identifying compounds that effect or affect Aβ processing; in one variation, the agents are thereby identified as candidate pharmaceutical agents. The transgenic animals can also be used to develop agents that modulate APP (or Aβ) expression and/or stability; such agents can serve as therapeutic agents to treat neurodegenerative diseases. The knockout animals of the invention can also serve as disease models for investigating APP-related pathological conditions (e.g., Alzheimer's disease and the like). Such transgenic animals can be commercially marketed to researchers, among other uses.

Antibodies for Swedish Mutation APP

Using APP polypeptides comprising the Swedish mutation, it is then possible to prepare antisera and monoclonal antibodies using, for example, the method of Kohler and Milstein ((1975) Nature 256: 495). Such monoclonal antibodies could then form the basis of a diagnostic test for the presence of the Swedish mutation, among other uses.

Swedish mutation APP polypeptides may be used to immunize an animal for the production of specific antibodies. These antibodies may comprise a polyclonal antiserum or may comprise a monoclonal antibody produced by hybridoma cells. For general methods to prepare antibodies, see Antibodies: A Laboratory Manual, (1988) E. Harlow and D. Lane, Cold Spring Harbor Laboratory, Cold Spring Harbor, N.Y., which is incorporated herein by reference.

For example but not for limitation, a recombinantly produced fragment of the Swedish mutation APP$^{695}$ polypeptide can be injected into a mouse along with an adjuvant so as to generate an immune response. Murine immunoglobulins which bind the recombinant fragment with a binding affinity of at least $1 \times 10^7$ M$^{-1}$ can be harvested from the immunized mouse as an antiserum, and may be further purified by affinity chromatography or other means. Additionally, spleen cells are harvested from the mouse and fused to myeloma cells to produce a bank of antib dy-secreting hybridoma cells. The bank of hybridomas can be screened for clones that secrete immunoglobulins which bind the recombinantly produced fragment with an affinity of at least $1 \times 10^6$ M$^{-1}$. More specifically, immunoglobulins that bind to the Swedish mutation APP polypeptide but have limited crossreactivity with a wild-type APP polypeptide are selected, either by preabsorption with wild-type APP or by screening of hybridoma cell lines for specific idiotypes that preferentially bind the Swedish mutation variant as compared to the wild-type.

The following examples are provided for illustration and are not intended to limit the invention to the specific example provided.

EXPERIMENTAL EXAMPLES

Antibody 6C6 recognizes an epitope within residues 1–16 of βAP.

Transgenic Mice Expresssing Swedish Mutation APP

Figure 1B:
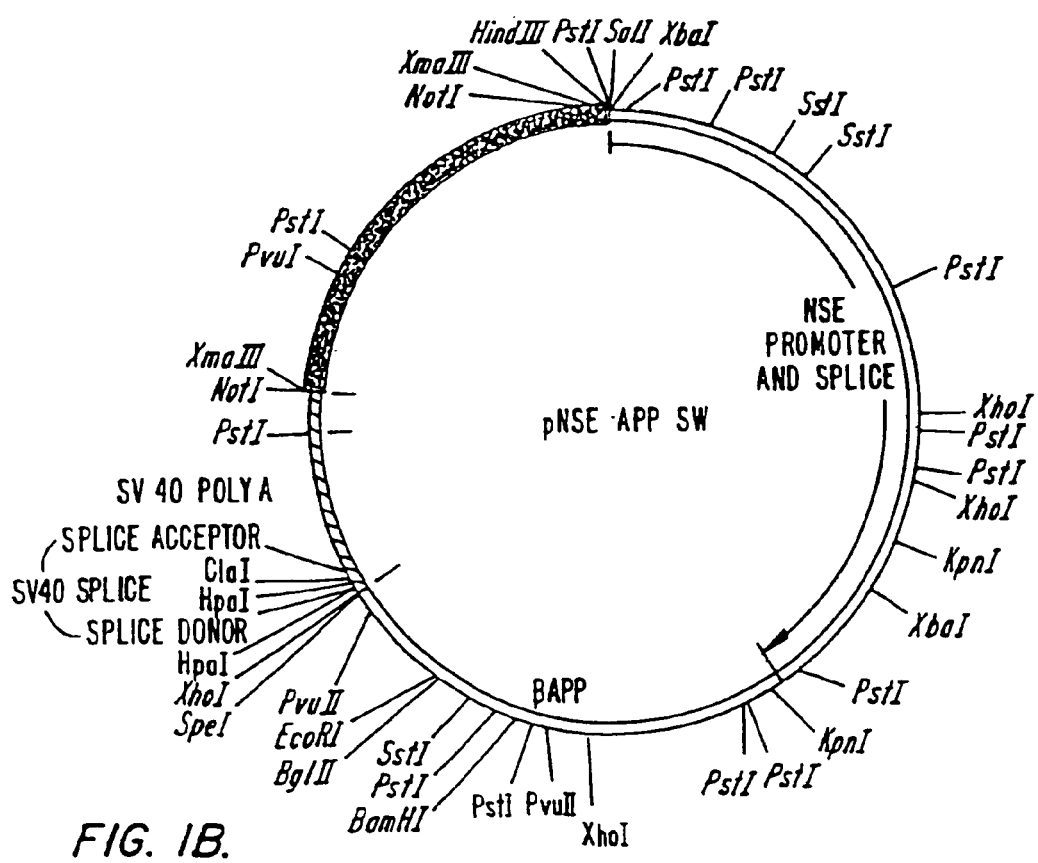

Transgenic mice were generated using the plasmids shown in FIG. 1 (NSEAPPsw and NSEAPPswΔ3'). These plasmids contain the 751 form of βAPP containing the Swedish mutation (KM to NL at position 595 and 596 of the 695 form). The neural-specific enolase promoter drives expression and provides a splice sequence. The rat NSE promoter and splice sequences were derived from pNSE6 (Forss-Petter et al. (1990) Neuron 5: 187). This vector contains the 4.2 kb BglII fragment of the rat NSE promoter region (starting from the upstream BglII site and continuing to the BglII site in the second intron) cloned into the BamHI sit of the vector pSP65 (Promega). The vector-derived XbaI site at the 5' end of the promoter used and the NSE translation initiating ATG, contained within the second intron, was fused to the βAPP-initiating ATG.

NSEAPPsw also contains a splice sequence from SV40 in the 3' region of the gene. This splice sequence was derived from the Okayama/Berg vector pL1, and is a fusion of the late 16s and 19s message splice sequences. Polyadenylation is provided by SV40 sequences.

Transgenic mice incorporating these plasmid sequences were generated using standard techniques. The NotI fragment containing the above described expression cassette was purified and injected into eggs obtained from a C57B1/DBA hybrid mouse. The eggs were implanted into pseudopregnant mice and the offspring were screened for expression of human βAPP by analysis of their F1 transgenic offspring. Brains from the F1 animals were homogenized with a handheld homogenizer (Polytron PT122B, Kinematica AG) either in SDS buffer (2% SDS, 20 mM Tris, pH 8.0, 150 mM NaCl, 10 mM EDTA) or homogenized in NP-40 buffer (1% NP40, 50 mM Tris, pH 7.5, 10 mM EDTA, and a cocktail of protease inhibitors containing 5–10 µg/ml leupeptin, 2–4 µg/ml Pepstatin A, 5–10 µg/ml Aprotinin, and 1–2 mM PMSF). The SDS lysates were loaded directly onto gels for Western analysis. The NP40 homogenates were spun at 44,000 rpm for 10 minutes in a Beckman ultracentrifuge (Tl100.3 rotor) and the supernatants were loaded onto gels for Western analysis. The Western analysis was done by standard procedures utilizing either anti-5 (0.4 µg/ml) or 8E5 (5 µg/ml) antibodies to detect the human specific βAPP. Those lines expressing relatively high levels of βAPP were chosen for further analysis. This included the lines Hillary 14, Chelsea 32 and Chelsea 58. The experiments described were done on heterozygote animals of these lines derived by breeding transgene-containing animals with wildtype animals and screening the offspring for presence of the transgene. Similarly, homozygous animals from a selected number of lines can be used.

Figure 2:
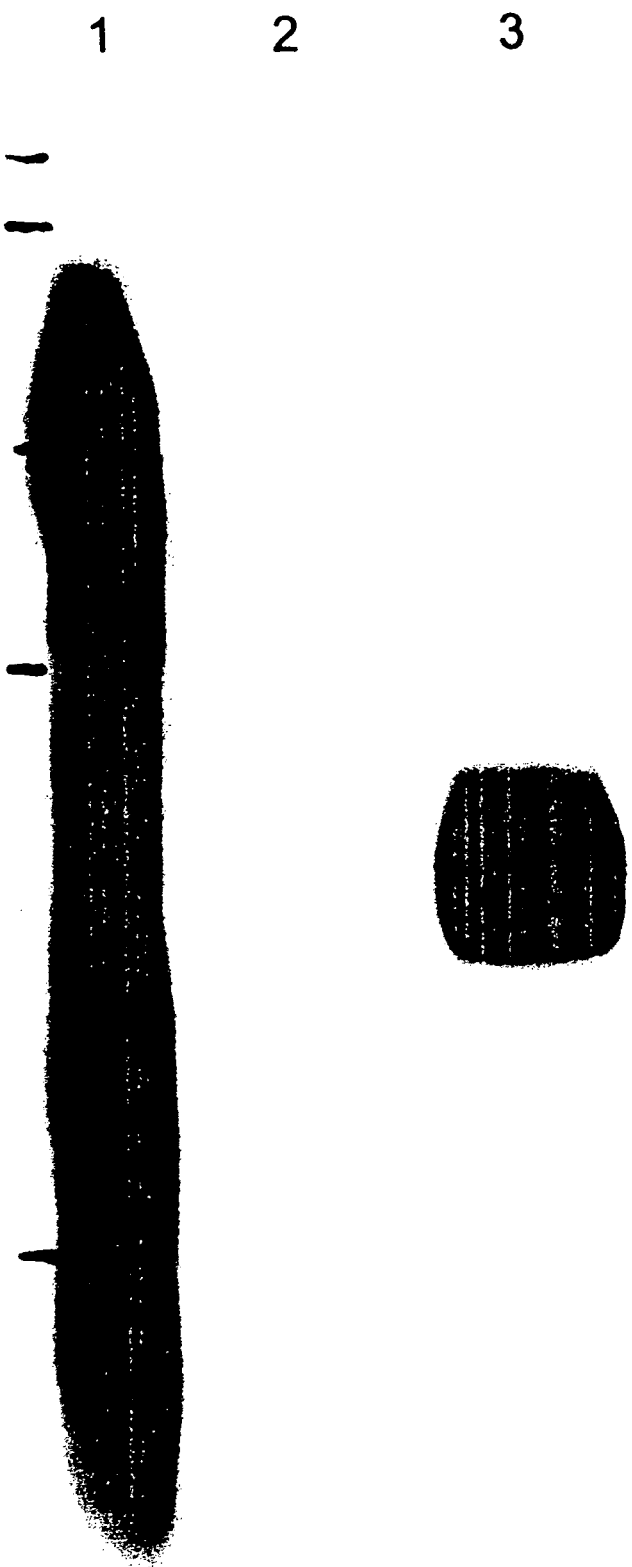
FIG. 2 is a Western blot of soluble fractions of transgenic and control animal brains probed for the presence of secreted βAPP fragments reactive with the Swedish 192 antibody. Lane 1: molecular weight markers; lane 2: non-transgenic line; lane 3: transgenic line.

Soluble fractions of transgenic animal brains were probed for the presence of the "92" form of the secreted APP (FIG. 2). This form is produced as a byproduct of the production of βAP and inhibition of the production of this form in cultured cells accompanies inhibition of the cleavage of the N-terminal end of βAP, the site cleaved by β-secretase.

Brains from transgenic (Swedish Hillary 14) or non-transgenic mice were homogenized in 50 mM Tris, 10 mM EDTA plus the above described protease inhibitor cocktail and centrifuged at 55K rpm for 10 min as described above. The supernatant was analyzed by Western utilizing the Swedish "192" antibody that reacts only with the secreted form of APP produced by β-secretase. For Western analysis proteins were separated on a 6% SDS PAGE gel (from Novex) and then transferred to immobilonP by standard techniques. The filter was incubated with 2 µg/ml of the Swedish "192" antibody again using standard techniques and the bound antibody visualized using the AmershamECL kit. As shown in FIG. 2, lane 3, there was robustly detectable "92" reactive material in the supernatant from the transgenic animal. The non-transgenic animal brain homogenate contained a low amount immunoreactive material that is slightly faster in mobility on the gel than the material specific to the transgenic animal (lane 1). This material is probably not related to βAPP since it does not hybridize with other βAPP antibodies (e.g., anti-5).

Figure 3A:
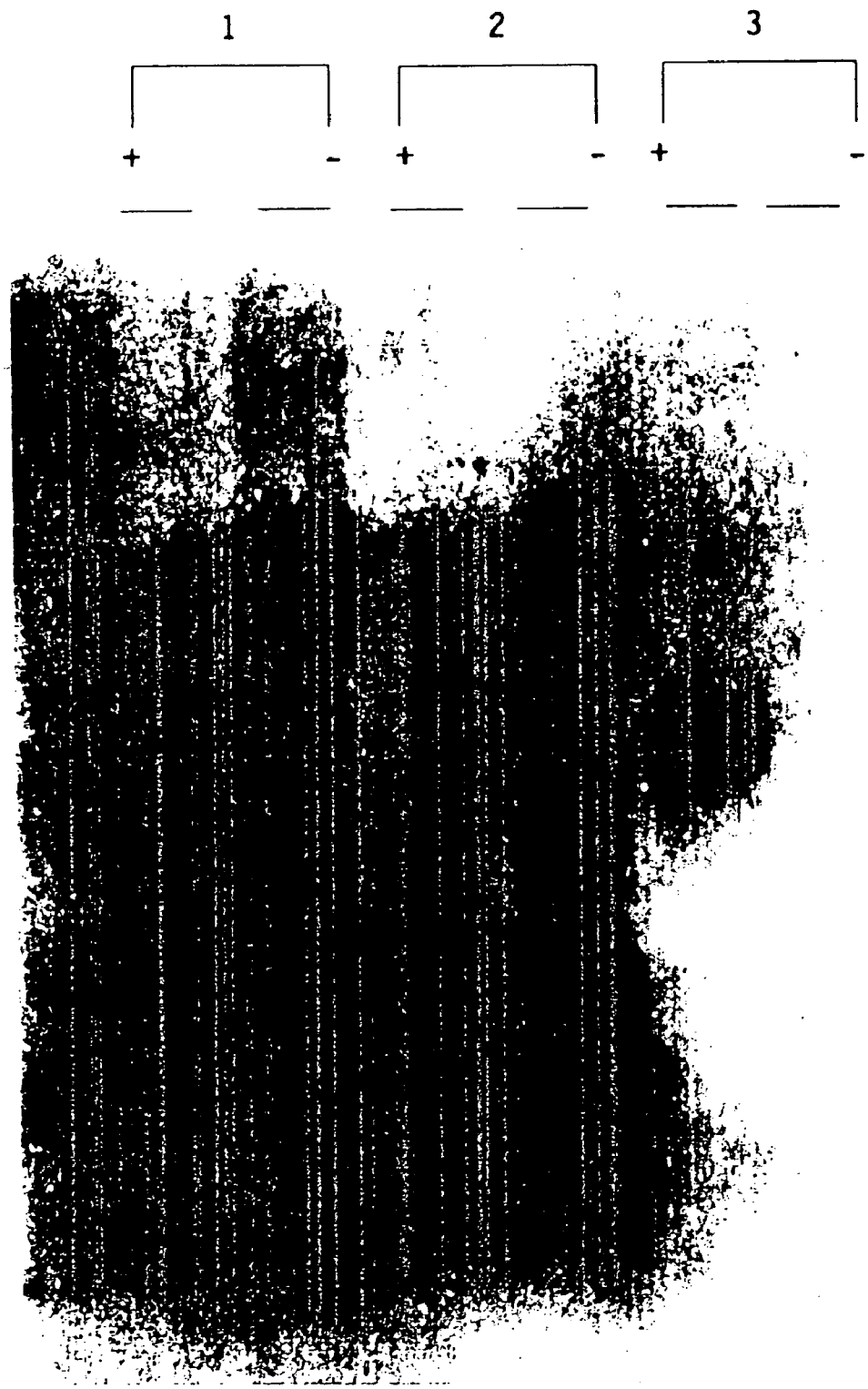
FIG. 3, panels A and B are Western blots of brain homogenates from transgenic (+) and non-transgenic (−) animals depleted of 6C6 antibody-reactive βAPP forms probed with antibody 8E5 (panel A) and Swedish 192 antibody (panel B).
Figure 3B:
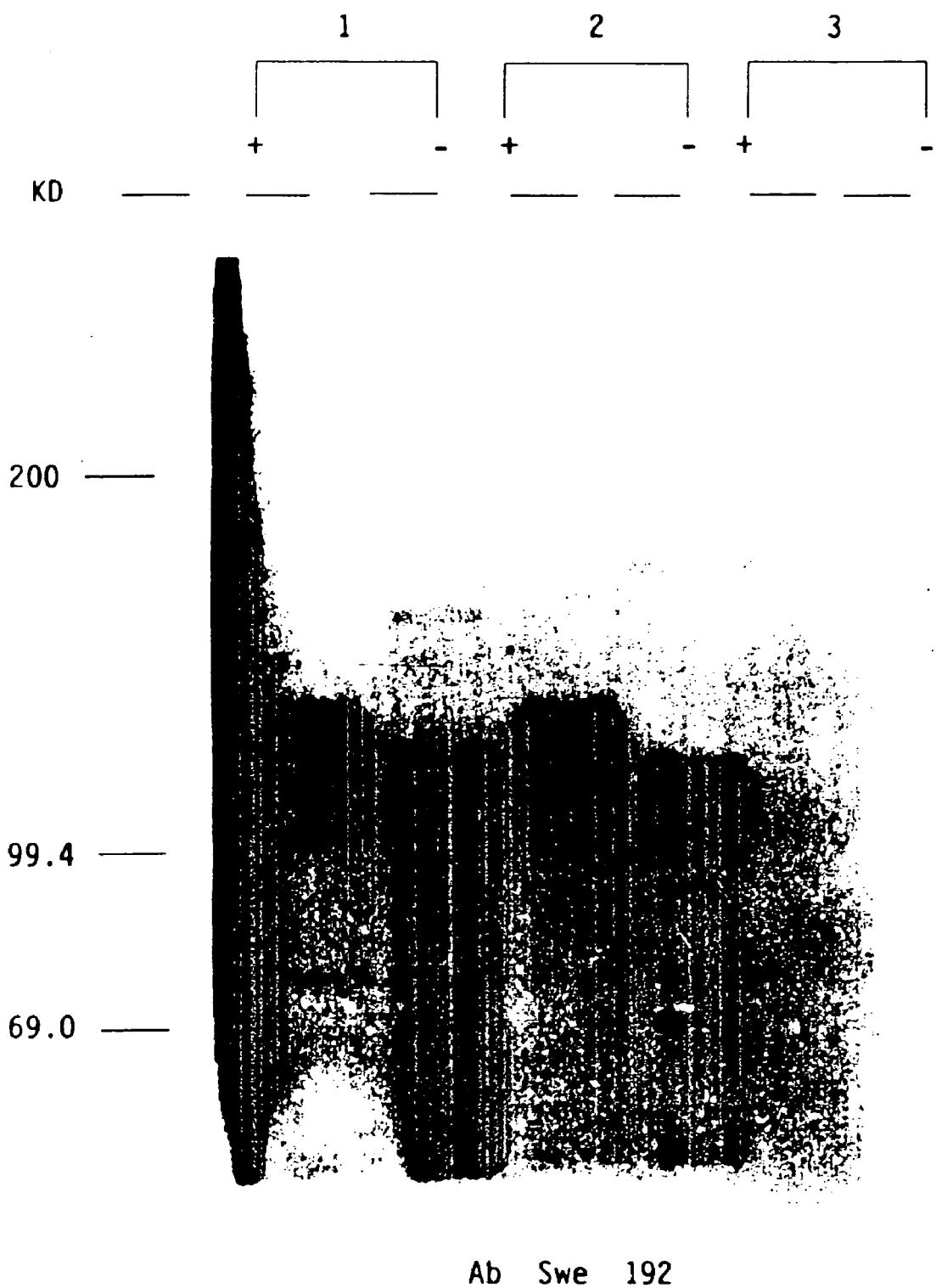

In tissue culture systems, the Swedish 192 antibody (infra) does not crossreact with secreted βAPP that is cleaved at the alpha-secretase site at position 17 in the middle of the β-peptide sequence. To prove that this is also true in the brain homogenates, brain homogenates were depleted of the longer secreted βAPP forms using resin bound to 6C6 antibody, which is specific for the first 16 amino acids of the βAP, and therefore reacts with alpha-secretase cleaved secreted βAPP but not with the shorter β-secretase cleaved secreted βAPP. Resin was produced by using Actigel-ALS coupled in suspension as described by the manufacturer (Sterogene). An excess of resin-antibody was incubated with the brain homogenates from animals either containing or not containing the transgene for an initial incubation of 3 hours at 4° C. with shaking, and bound and unbound material was separated by centrifugation at 14,000 rpm for 1 min. The supernatant was again incubated with an excess of 6C6 coupled resin for 16 hours at 4° C., and again centrifuged to separate the unbound material. Material that bound during the first incubation and material that did not bind to the 6C6 coupled resin were analyzed by Western utilizing anti-5 and Swedish 192 antibodies (FIG. 3). Homogenates from transgenic (+) or non-transgenic (−) mice were probed with 8E5 (panel A) or Swedish 192 (panel B). Lanes 1 refer to total homogenate, lanes 2 to the fraction that did not bind to the 6C6 resin and lanes 3 refer to the fraction that bound to the 6C6 coupled resin. None of the bound βAPP, identified by its reactivity to anti-5 antibody, crossreacted with the Swedish 192 antibody. Unbound material, identified by reactivity to anti-5, reacted with the Swedish 192 antibody.

This demonstrates that the Swedish mutation transgenic mouse provides a viable animal model for screening for direct or indirect inhibitors of β-secretase activity, or for drugs that modulate β-secretase activity. Such agents may be developed as pharmaceuticals for treating diseases associates with abnormal APP expression and/or metabolism (e.g., Alzheimer's disease).

Antibodies Specifically Reactive wih Swedish Mutation APP

Monoclonal antibody 6C6 was raised and screened in the same manner as antibody 10D5 (Hyman et al. (1992) *J. Neuropath. Exp. Neurol.* 51: 76) using a synthetic peptide containing βAP residues 1–28 conjugated to rabbit serum albumin as the immunogen. Both 10D5 and 6C6 recognize an epitope within the first 16 amino acids of the βAP sequence. 6C6 was more efficient than 10D5 in immunoprecipitation and was used as a capture antibody. To prepare 6C6 resin, 4 mls of Affigel®10 (Bio-Rad Laboratories, Hercules, Calif.) was washed with cold water and combined with 3 mls of 6C6 (12.5 mg/ml in PBS (2.7 mM KCl, 1.5 mM $KH_2PO_4$, 8.1 mM $Na_2HPO_4$, 137 mM NaCl, pH 7.5) 0.5 M NaCl. The coupling proceeded overnight at 4° C. with gentle shaking. 400 µl of 1M Tris, pH 8.0, was then added, and shaking was continued for 40 minutes. The resin was then washed with TTBS (137 mM NaCl, 5 mM KCl, 25 mM Tris, 0.5% Tween®20, pH 7.5) exhaustively before use. Antibody 7H5 is also described in Hyman et al. (1992), supra. Anti-5 antibodies were raised against βAPP 444–592.

Antibodies (designated antibody 92) were raised against a synthetic peptide including residues 591–596 of βAPP (as numbered in Kang et al. (1987), supra). The peptide (N-acetyl-CISEVKM) was conjugated to rabbit serum albumin which had been activated with sulfo-maleimido benzoyl-N-hydroxysuccinimide ester to form an immunogen. Antisera were raised against the immunogen in rabbits by standard methodologies. During each inoculation, rabbits received 5 µg of immunogen in 0.1 ml injections subcutaneously at approximately 10 sites (50 µg/boost). The same peptide was coupled to Sulfo-link™ gel (Pierce Chemical Co., Rockford, Ill.) for the affinity purification of antibodies from the IgG fraction.

A more detailed description of the antibody 92 preparation is as follows. Rabbit serum albumin (12.3 mg) was incubated with 13 mg of sulfo-maleimido benzoyl-N-hydroxysuccinimide ester in 1.25 mls of 0.05 M $KH_2PO_4$, pH 7.0 for 20 minutes at 0° C. The mixture was then immediately subjected to gel filtration on a 1×75 cm column of Sephadex G-10 equilibrated with the phosphate buffer. The protein eluant in the excluded volume was pooled and immediately combined with 30 mg of N-acetyl-CISEVKM peptide which was synthesized by standard automated solid phase methodologies. The coupling reaction (20 ml volume) was allowed to proceed overnight and was then sent to a commercial facility for antibody generation. The injection protocol was to emulsify the antigen in an equal volume of Freund's complete adjuvant and subcutaneously inject a total of 50 µg of antigen in 0.1 ml aliquots in approximately 10 sites. Every three weeks thereafter, a booster injection was given by an identical protocol except Freund's incomplete adjuvant was used as the emulsifier. Rabbits were bled one week following each injection and the serum examined for titer by reaction to peptide in ELISA. The IgG was purified from the positive reacting sera by precipitation with 50% $(NH_4)_2SO_4$, (2×'s) and dialyzed against PBS. The N-acetyl-CISEVKM peptide was conjugated to Sulfo-link™ gel (Pierce Chemical Co., Rockford, Ill.) using the manufacturer's recommendations to generate an affinity resin to purify the peptide specific antibodies. The IgG fraction was applied to the column and, after washing through non-specifically bound material with PBS, the antibodies were eluted with 0.1 M glycine pH 2.5 0.5 M NaCl and then dialyzed vs PBS before freezing.

Swedish 192 antibody was raised against a synthetic peptide composed of residues 590–596 of the Swedish βAPP sequence. In addition to the βAPP sequence, two glycines and a cysteine were added as a spacer and a linker giving the following sequence: CGGEISEVNL. The peptide was conjugated to a commercially available maleimide activated cationized Bovine Serum Albumin (Pierce Imject Supercarrier Immune Modulator, hereafter referred to as cBSA.) Antiserum was raised by following the injection schedule described above for antibody 92.

Antibody Swedish 192 was raised against a synthetic peptide composed of residues 590–596 of the Swedish βAPP sequence. In addition to the βAPP sequence two glycines and a cysteine were added as a spacer and a linker giving the following sequence: CGGEISEVNK. The peptide was conjugated to a commercially available maleimide activated cationized Bovine Serum Albumin (Pierce Imject Supercarrier immune Modulator, hereafter referred to as cBSA.) Antiserum was raised by following a standard injection schedule.

In general, cBSA was resuspended in deionized water to a concentration of 10 mg/ml. An equal milligram amount of peptide was added to the carrier and mixed for four hours at room temperature. The conjugate was then dialyzed extensively against Dulbecco's Phosphate Buffered Saline without calcium and magnesium.

The conjugate was compared to the starting cBSA on a 6% Novex pre-poured Tris-glycine gel. Successful conjugation was indicated by a visible shift to a higher molecular weight.

Conditioned medium from 293 kidney cells, which have been stably transfected to overexpress the Swedish βAPP protein, was collected. One milliliter aliquots were added to either 100 µl of immobilized 6C6-affinity resin or 100 µl of heparin agarose (Sigma). The reaction with the 6C6 resin was for 5 hours at 4° C.; the heparin-agarose was reacted for 30 minutes at 4° C. After incubation, the resins were washed with TTBS and then 100 µl of 2×SDS-PAGE sample buffer were added to each sample, the samples were boiled (5 minutes) and briefly centrifuged. Twenty µl of the samples were loaded onto 6% SDS-polyacrylamide gels and electrophoresed. The proteins were transferred to ProBlot membranes as described above. The samples were probed with the following antibodies: 6C6, Swedish 192, or 8E5 (a monoclonal antibody which recognizes an epitope of βAPP in the region of amino acids 444–592, using the numbering of the 695 form.) All antibodies were used at 2 µg/ml during the probing of the immunoblot. The visualization of immunoreactive material was achieved using the Amersham ECL® system according to the manufacturer's recommendations. Blocking and antibody dilutions were made using 5% non-fat dry milk (Carnation) in TTBS.

Figure 4:
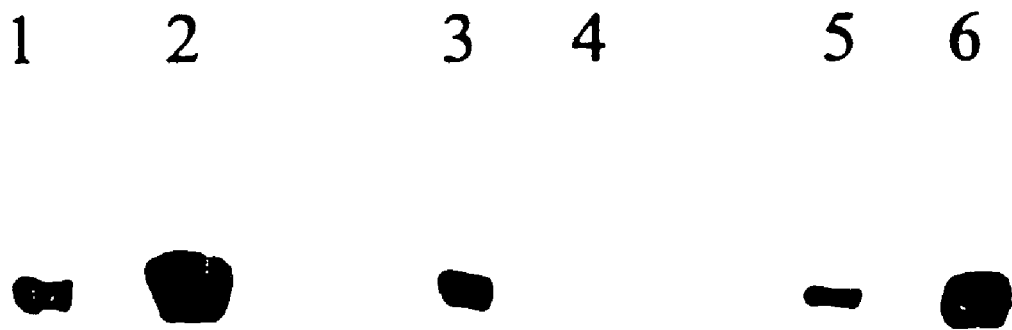
FIG. 4 shows an immunoblot demonstrating specificity of the Swedish 192 antibody. Lanes 1, 3, 5 contain material eluted from heparin agarose. Lanes 2, 4, 6 contain material eluted from the 6C6 resin. Lanes 1 and 2 were probed with antibody 8E5; Lanes 3 and 4 were probed with the Swedish 192 antibody; Lanes 5 and 6 were probed with antibody 6C6.

FIG. 4 shows an immunoblot demonstrating specificity of the Swedish 192 antibody. Lanes 1, 3, 5 contain material eluted from heparin agarose. Lanes 2, 4, 6 contain material eluted from the 6C6 resin. Lanes 1 and 2 were probed with antibody 8E5; Lanes 3 and 4 were probed with the Swedish 192 antibody; Lanes 5 and 6 were probed with antibody 6C6.

As can be seen in FIG. 4, lane 4, the Swedish 192 antibody does not appreciably recognize the 6C6 reactive form of βAPP despite the fact that more total βAPP is present in lane 4 compared to lane 3 (compare lanes 1 and 2). The lack of reactivity with βAPP forms containing the partial βAP sequence (6C6-reactive) suggests the Swedish 192 antibody recognizes βAPP cleaved at or near the amino-terminus of Aβ.

The foregoing description of the preferred embodiments of the present invention has been presented for purposes of illustration and description. They are not intended to be exhaustive or to limit the invention to the precise form disclosed, and many modifications and variations are possible in light of the above teaching.

Such modifications and variations which may be apparent to a person skilled in the art are intended to be within the scope of this invention.

All publications and patent applications herein are incorporated by reference to the same extent as if each individual publication or patent application was specifically and individually indicated to be incorporated by reference.

The invention claimed is:

1. A method of preparing a composition comprising an agent that affects processing of amyloid precursor protein to beta-amyloid peptide, the method comprising:
    providing a transgenic rodent comprising a diploid genome comprising a comprising in operable linkage a promoter and a DNA segment encoding a human APP polypeptide comprising the Swedish mutation wherein the amino acid residues aat positions corresopnding to positions 595 and 596 in human $APP^{695}$ are asparaagine and leucine, respectively, wherein the transgene is expressed to produced a human APP polypeptide having the Swedish mutaation, and wherein the polypeptide is processed to ATF-βAPP in a sufficient amount to be detectable in a brain homogenate of said transgenic rodent;
    contacting the transgenic rodent with the agent;
    monitoring cleavage of the amyloid precursor protein polypeptide between the N-terminus of the beta amyloid peptide and the ATF-βAPP in the contacted transgenic rodent compared to the cleavage in a control transgenic rodent to indicate the agent affects the cleavage; and incorporating the agent into a composition with a pharmaceutical carrier.

2. The method of claim 1, wherein the rodent is murine.

3. The method of claim 1, wherein the rodent is a mouse.

4. The method of claim 1, wherein the transgene is nonhomologously integrated.

5. The method of claim 1, wherein the promoter is a neural specific enolase promoter.

6. The method of claim 1, wherein the agent inhibits a beta-secretase activity associated with the cleavage.

7. The method of claim 1, wherein the dosage of the agent is from 10 µg/kg to 1 mg/kg.

* * * * *